(12) United States Patent
Lajeunesse et al.

(10) Patent No.: US 7,491,725 B2
(45) Date of Patent: Feb. 17, 2009

(54) PROCESS FOR PREPARING 2-AMINOTHIAZOLE-5-AROMATIC CARBOXAMIDES AS KINASE INHIBITORS

(75) Inventors: Jean Lajeunesse, Candiac (CA); John D. DiMarco, East Brunswick, NJ (US); Michael Galella, Kendall Park, NJ (US); Ramakrishnan Chidambaram, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 251 days.

(21) Appl. No.: 11/192,867

(22) Filed: Jul. 29, 2005

(65) Prior Publication Data

US 2006/0004067 A1      Jan. 5, 2006

Related U.S. Application Data

(63) Continuation-in-part of application No. 11/051,208, filed on Feb. 4, 2005, now abandoned.

(60) Provisional application No. 60/542,490, filed on Feb. 6, 2004, provisional application No. 60/624,937, filed on Nov. 4, 2004, provisional application No. 60/649,722, filed on Feb. 3, 2005.

(51) Int. Cl.
*A61K 31/506* (2006.01)
*C07D 403/04* (2006.01)

(52) U.S. Cl. ................. 514/252.19; 544/295

(58) Field of Classification Search ............. 544/295; 514/252.19

See application file for complete search history.

(56) References Cited

U.S. PATENT DOCUMENTS

| | | | |
|---|---|---|---|
| 3,547,917 | A | 12/1970 | Kulka et al. |
| 5,114,940 | A * | 5/1992 | Blade et al. ............ 514/248 |
| 6,596,746 | B1 | 7/2003 | Das et al. |
| 2004/0024208 | A1 | 2/2004 | Das et al. |
| 2004/0054186 | A1 | 3/2004 | Das et al. |
| 2004/0073026 | A1 | 4/2004 | Das et al. |
| 2004/0077875 | A1 | 4/2004 | Das et al. |
| 2004/0220233 | A1 | 11/2004 | Hynes et al. |
| 2005/0009891 | A1 | 1/2005 | Lee |
| 2005/0215795 | A1 | 9/2005 | Chen et al. |

FOREIGN PATENT DOCUMENTS

| | | |
|---|---|---|
| EP | 639574 | 2/1995 |
| WO | WO 0062778 | 10/2000 |
| WO | WO 2004071440 | 8/2004 |
| WO | WO 2004085388 | 10/2004 |
| WO | WO 2005013983 | 2/2005 |
| WO | WO2005/072826 | 8/2005 |

OTHER PUBLICATIONS

Byrn et al. (Sold-State Chemistry of Drugs, 2nd Edition, 1999, SSCI, Inc. Publishers).*
U.S. Appl. No. 11/049,815, filed Feb. 3, 2005, Chen et al.
Autenrieth, W., "Regarding our knowledge of the five isomeric acids $C_4H_6O_2$", Chem. Ber., vol. 38, pp. 2534-2551, *English Translation*.
Eremeev et al., "Absolute Configuration of Diastereomeric Derivatives of N-Substituted Aziridine-2-Carboxylic Acids", Chem. Heterocycl. Compd. Engl. Transl., vol. 20, pp. 1102-1107, 1984 (translated from Khimiya Geterotsiklicheskikh Soedinenii, No. 10, pp. 1342-1348, 1984).
Hartmann et al., "On the coupling of aryldiazonium salts with *N,N*-disubstituted 2-aminothiophenes and some of their carbocyclic and heterocyclic analogues", J. Chem. Soc.; Perkin Trans. vol. 1, pp 4316-4320, 2000.
Kantlehner et al., "Ein neues Herstellungsverfahren für 2,2,2-Trialkoxyacetonitrile und 2-Dialkylamino-2-alkoxycarbonsäurenitrile", Synthesis, pp. 358-360, 1984.
Kantlehner et al., "Orthoamides. IL Reaction of Orthoamide Derivatives with Sulfur and Selenium, Syntheses of 1,3-Thiazole- and 1,3-Selenazole Derivatives", J. prakt. Chem., vol. 338, pp. 403-413, 1996.
Knoll et al., "Formylation Products of Thioamides; VII[1]. Synthesis of New *N*-(3-AMinothioacryloyl)-formamidines and *N,N*'-Bis[aminomethylidene]thioureas by Bis-iminoformylation of Thioacetamides and Thiourea with Formamide Acetals", Synthesis Communications, pp. 51-53, 1984.
Landreau et al., "[4+2] Cycloaddition Reactions Between 2,4-Diamino-1-Thia-3-Azabutadienes and Ketene. Synthesis of New 1,3-Thiazin-6-ones, 1,3-Thiazine-6-Thiones and 2-Thioxopyrimidin-4-ones", Heterocycles, vol. 53, No. 12, pp. 2667-2677, 2000.

(Continued)

*Primary Examiner*—Kamal A Saeed
*Assistant Examiner*—Jason Nolan
(74) *Attorney, Agent, or Firm*—Mary K. VanAtten

(57) ABSTRACT

The invention relates to processes for preparing compounds having the formula,

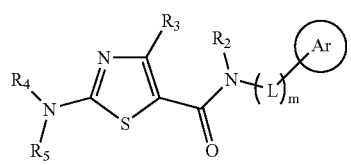

and crystalline forms thereof, wherein Ar is aryl or heteroaryl, L is an optional alkylene linker, and $R_2$, $R_3$, $R_4$, and $R_5$, are as defined in the specification herein, which compounds are useful as kinase inhibitors, in particular, inhibitors of protein tyrosine kinase and p38 kinase.

16 Claims, 7 Drawing Sheets

OTHER PUBLICATIONS

Landreau et al., "Cationic 1,3-Diazadienes in Annulation Reactions. Synthesis of Pyrimidine, Thiadiazinedioxide and Triazine Derivatives", J. Heterocyclic Chem., vol. 38, pp. 93-98, 2001.

Lin et al., "The Synthesis of Substituted 2-Aminothiazoles", J. Heterocyclic Chem., vol. 16, pp. 1377-1383, 1979.

Marsham et al., "Quinazoline Antifolate Thymidylate Synthase Inhibitors: Heterocyclic Benzoyl Ring Modifications", J. Med. Chem., vol. 34, pp. 1594-1605, 1991.

Noack et al., "Synthesis and characterization of N,N-disubstituted 2-amino-5-acylthiophenes and 2-amino-5-acylthiazoles", Tetrahedron, vol. 58, pp. 2137-2146, 2002.

Noack et al., "Synthesis and Spectral Characterisation of a New Class of Heterocyclic Analogues of Crystal Violet Dyes", Angew. Chem. Int. Ed., vol. 113, No. 16, pp. 3008-3011, 2001.

Roberts et al., "Folic Acid Analogs. Modifications in the Benzene-Ring Region. 2. Thiazole Analogs", J. Medicinal Chemistry, vol. 15, No. 12, pp. 1310-1312, 1972.

Zhao et al., "A new facile synthesis of 2-aminothiazole-5-carboxylates", Tetrahedron Letters, vol. 42, pp. 2101-2102, 2001.

Shah et al., "Overriding Imatinib Resistance with a Novel ABL Kinase Inhibitor", Science, vol. 35, pp. 339-401, 2004.

U.S. Appl. No. 11/271,626, Office Action Jan. 31, 2008.

* cited by examiner

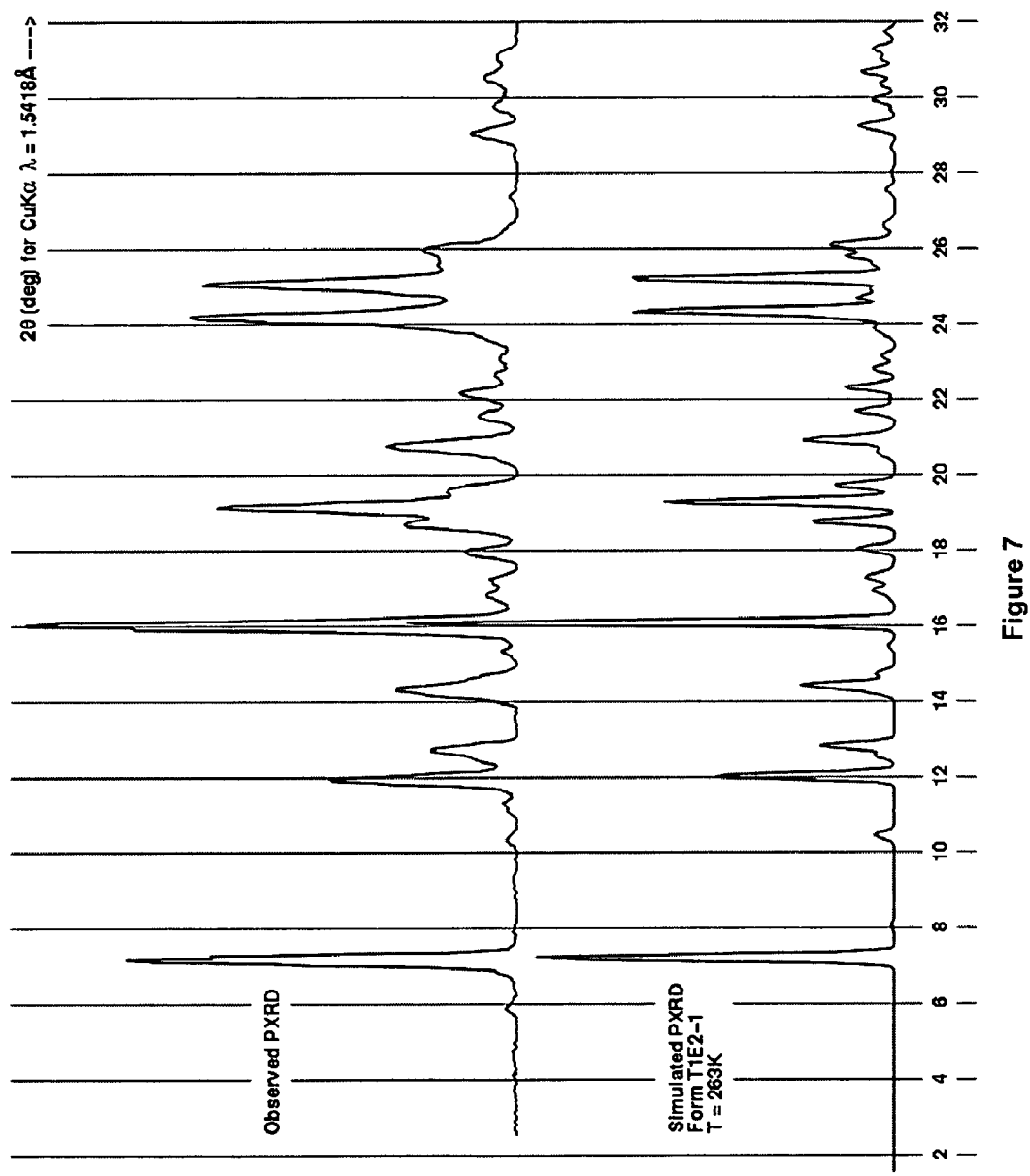

PROCESS FOR PREPARING 2-AMINOTHIAZOLE-5-AROMATIC CARBOXAMIDES AS KINASE INHIBITORS

CROSS-REFERENCE TO RELATED APPLICATIONS

This application is a continuation-in-part of U.S. Non-Provisional Application Ser. No. 11/051,208, filed Feb. 4, 2005 now abandoned, which claims the benefit of U.S. Provisional Application No. 60/542,490, filed Feb. 6, 2004, U.S. Provisional Application No. 60/624,937, filed Nov. 4, 2004 and U.S. Provisional Application No. 60/649,722, filed Feb. 3, 2005, which are all hereby incorporated by reference in their entirety.

FIELD OF THE INVENTION

The present invention relates to processes for preparing 2-aminothiazole-5aromatic carboxamides which are useful as kinase inhibitors, such as inhibitors of protein tyrosine kinase and p38 kinase, intermediates and crystalline forms thereof.

BACKGROUND OF THE INVENTION

Aminothiazole-aromatic amides of formula I

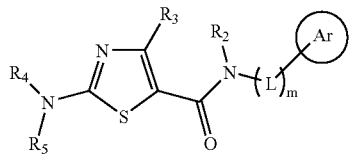

wherein Ar is aryl or heteroaryl, L is an optional alkylene linker, and $R_2$, $R_3$, $R_4$, and $R_5$, are as defined in the specification herein, are useful as kinase inhibitors, in particular, inhibitors of protein tyrosine kinase and p38 kinase. They are expected to be useful in the treatment of protein tyrosine kinase-associated disorders such as immunologic and oncological disorders [see, U.S. Pat. No. 6,596,746 (the '746 patent), assigned to the present assignee and incorporated herein by reference], and p38 kinase-associated conditions such as inflammatory and immune conditions, as described in U.S. patent application Ser. No. 10/773,790, filed Feb. 6, 2004, claiming priority to U.S. Provisional application Ser. No. 60/445,410, filed Feb. 6, 2003 (hereinafter the '410 application), both of which are also assigned to the present assignee and incorporated herein by reference.

The compound of formula (IV), 'N-(2-Chloro-6-methylphenyl)-2-[[6-[4-(2-hydroxyethyl)-1-piperazinyl]-2-methyl-4-pyrimidinyl]amino]-5-thiazolecarboxamide, is an inhibitor of SRC/ABL and is useful in the treatment of oncological diseases.

(IV)

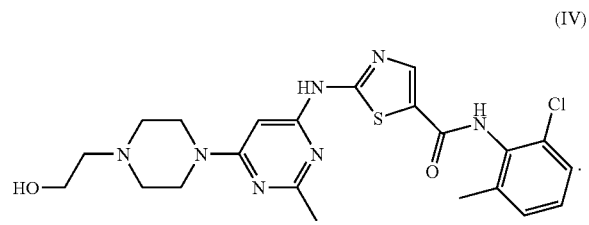

Other approaches to preparing 2-aminothiazole-5-carboxamides are described in the '746 patent and in the '410 application. The '746 patent describes a process involving treatment of chlorothiazole with n-BuLi followed by reaction with phenyl isocyanates to give chlorothiazole-benzamides, which are further elaborated to aminothiazole-benzamide final products after protection, chloro-to-amino substitution, and deprotection, e.g.,

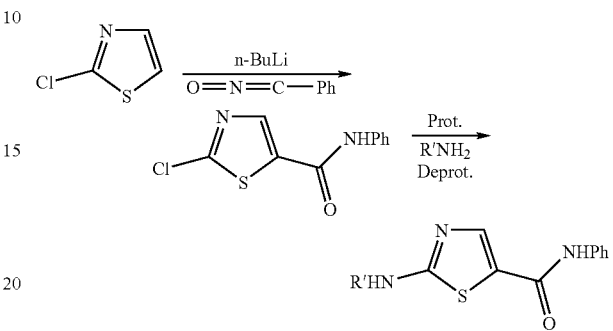

The '410 application describes a multi-step process involving first, converting N-unsubstituted aminothiazole carboxylic acid methyl or ethyl esters to bromothiazole carboxylic acid esters via diazotization with tert-butyl nitrite and subsequent $CuBr_2$ treatment, e.g.,

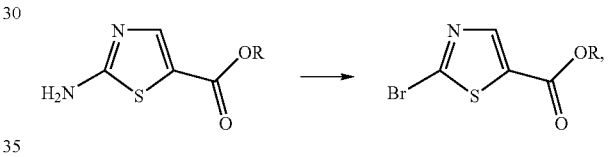

then, hydrolyzing the resulting bromothiazole esters to the corresponding carboxylic acids and converting the acids to the corresponding acyl chlorides, e.g.,

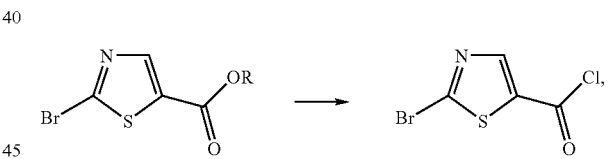

then finally, coupling the acyl chlorides with anilines to afford bromothiazole-benzamide intermediates which were further elaborated to aminothiazole-benzamide final products, e.g.,

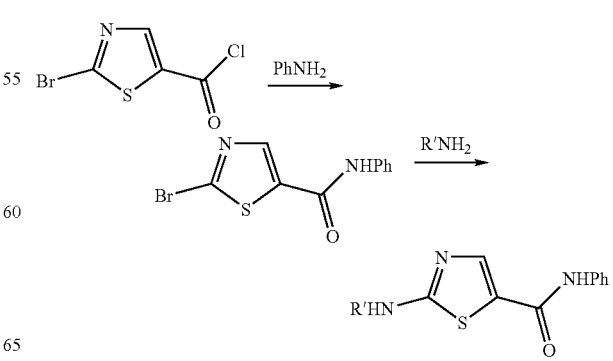

Other approaches for making 2-aminothiazole-5-carboxamides include coupling of 2-aminothiazole-5-carboxylic acids with amines using various coupling conditions such as DCC [Roberts et al, *J. Med. Chem.* (1972), 15, at p. 1310], and DPPA [Marsham et al., *J. Med. Chem.* (1991), 34, at p. 1594)].

The above methods present drawbacks with respect to the production of side products, the use of expensive coupling reagents, less than desirable yields, and the need for multiple reaction steps to achieve the 2-aminothiazole-5-carboxamide compounds.

Reaction of N,N-dimethyl-N'-(aminothiocarbonyl)-formamidines with α-haloketones and esters to give 5-carbonyl-2-aminothiazoles has been reported. See Lin, Y. et al, *J. Heterocycl. Chem.* (1979), 16, at 1377; Hartmann, H. et al, *J. Chem. Soc. Perkin Trans.* (2000), 1, at 4316; Noack, A. et al; *Tetrahedron* (2002), 58, at 2137; Noack, A.; et al. *Angew. Chem.* (2001), 113, at 3097; and Kantlehner, W. et al., *J. Prakt. Chem./Chem.-Ztg.* (1996), 338, at 403. Reaction of β-ethoxy acrylates and thioureas to prepare 2-aminothiazole-5-carboxylates also has been reported. See Zhao, R., et al., *Tetrahedron Lett.* (2001), 42, at 2101. However, electrophilic bromination of acrylanilide and crotonanilide has been known to undergo both aromatic bromination and addition to the α,β-unsaturated carbon-carbon double bonds. See Autenrieth, *Chem. Ber.* (1905), 38, at 2550; Eremeev et al., *Chem. Heterocycl. Compd. Engl. Transl.* (1984), 20, at 1102.

New and efficient processes for preparing 2-aminothiazole-5-carboxamides are desired.

SUMMARY OF THE INVENTION

This invention is related to processes for the preparation of 2-aminothiazole-5-aromatic amides having the formula (I)

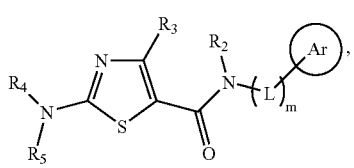

wherein L, Ar, $R_2$, $R_3$, $R_4$, $R_5$, and m are as defined below, comprising reacting a compound having the formula (II),

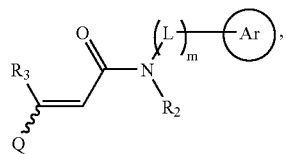

wherein Q is the group —O—P*, wherein P* is selected so that, when considered together with the oxygen atom to which P* is attached, Q is a leaving group, and Ar, L, $R_2$, $R_3$, and m are as defined below, with a halogenating reagent in the presence of water followed by a thiourea compound having the formula (III),

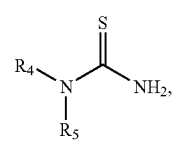

wherein, $R_4$ and $R_5$ are as defined below, to provide the compound of formula (I),

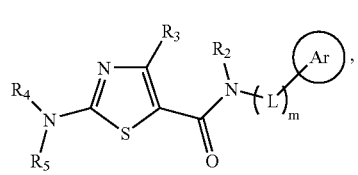

wherein,

Ar is the same in formulae (I) and (II) and is aryl or heteroaryl;

L is the same in formulae (I) and (II) and is optionally-substituted alkylene;

$R_2$ is the same in formulae (I) and (II), and is selected from hydrogen, alkyl, substituted alkyl, alkenyl, substituted alkenyl, alkynyl, substituted alkynyl, aryl, heteroaryl, cycloalkyl, and heterocyclo;

$R_3$ is the same in formulae (I) and (II), and is selected from hydrogen, halogen, cyano, haloalkyl, alkyl, substituted alkyl, alkenyl, substituted alkenyl, aryl, heteroaryl, cycloalkyl, and heterocyclo;

$R_4$ is (i) the same in each of formulae (I) and (III), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_4$ is taken together with $R_5$, to form heteroaryl or heterocyclo;

$R_5$ is (i) the same in each of formulae (I) and (III), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_5$ is taken together with $R_4$, to form heteroaryl or heterocyclo; and m is 0 or 1.

Applicants have surprisingly discovered said process for converting β-(P*)oxy acryl aromatic amides and thioureas to 2-aminothiazole derivatives, wherein the aromatic amides are not subject to further halogenation producing other side products. Aminothiazole-aromatic amides, particularly, 2-aminothiazole-5-benzamides, can thus be efficiently prepared with this process in high yield.

In another aspect, the present invention is directed to crystalline forms of the compound of formula (IV).

BRIEF DESCRIPTION OF THE DRAWINGS

The invention is illustrated by reference to the accompanying drawings described below.

FIG. 7 shows a simulated (bottom) (from atomic parameters refined at room temperature) and experimental (top) pXRD patterns for ethanolate form (T1E2-1) of the compound of formula (IV).

DETAILED DESCRIPTION OF THE INVENTION

Abbreviations

Figure 1:
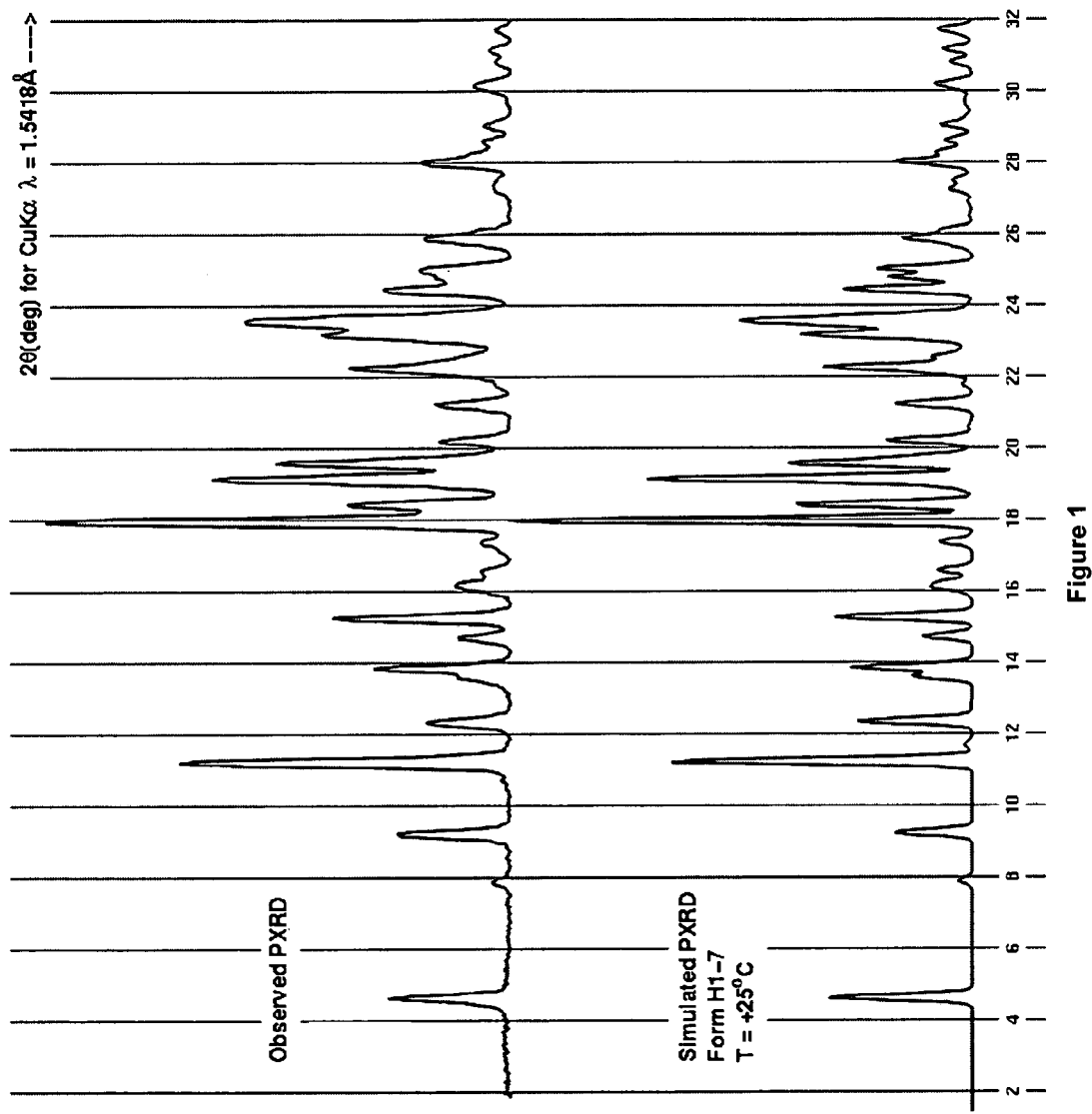
FIG. 1 shows a simulated (bottom) (calculated from atomic coordinates generated at room temperature) and experimental (top) pXRD patterns for crystalline monohydrate of the compound of formula (IV).

For ease of reference, the following abbreviations may be used herein:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DMF=dimethyl formamide
DMF-DMA=N,N-dimethylformamide dimethyl acetal
DMSO=dimethyl sulfoxide
DPPA=diphenylphosphoryl azide
DPPF=1,1'-bis(diphenylphosphino)ferrocene
HATU=O-benzotriazol-1-yl0 N,N,N',N'-tetramethyluronium hexafluorphosphate
LDA=lithium di-isopropyl amide
TEA=triethylamine
TFA=trifluoroacetic acid
THF=tetrahydrofuran
KOH=potassium hydroxide
$K_2CO_3$=potassium carbonate
$POCl_3$=phosphorous oxychloride
EDC or EDCI=3-ethyl-3'-(dimethylamino)propyl-carbodiimide
DIPEA=diisopropylethylamine
HOBt=1-hydroxybenzotriazole hydrate
NBS=N-bromosuccinamide
NMP=N-methyl-2-pyrrolidinone
NaH=sodium hydride
NaOH=sodium hydroxide
$Na_2S_2O_3$=sodium thiosulfate
Pd=palladium
Pd—C or Pd/C=palladium on carbon
min=minute(s)
L=liter
mL=milliliter
μL=microliter
g=gram(s)
mg=milligram(s)
mol=moles
mmol=millimole(s)
meq=milliequivalent
RT or rt=room temperature
RBF=round bottom flask
ret. t.=HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point
DSC=differential scanning calorimetry
TGA=thermogravimetric analysis
XRPD=x-ray powder diffraction pattern
pXRD=x-ray powder diffraction pattern Definitions The following are definitions of terms used in this specification and appended claims. The initial definition provided for a group or term herein applies to that group or term throughout the specification and claims, individually or as part of another group, unless otherwise indicated.

The term "alkyl" as used herein by itself or as part of another group refers to straight and branched chain saturated hydrocarbons, containing 1 to 20 carbons, 1 to 10 carbons, or 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms.

The term "substituted alkyl" refers to an alkyl group substituted with one or more substituents (for example 1 to 4 substituents, or 1 to 2 substituents) at any available point of attachment. Exemplary substituents may be selected from one or more (or 1 to 3) of the following groups:

(i) halogen (e.g., a single halo substituent or multiple halo substitutents forming, in the latter case, groups such as a perfluoroalkyl group or an alkyl group bearing $Cl_3$ or $CF_3$), haloalkoxy, cyano, nitro, oxo (=O), —$OR_a$, —$SR_a$, —S(=O)$R_e$, —S(=O)$_2R_e$, —S(=O)$_3H$, —P(=O)$_2$—$R_e$, —S(=O)$_2OR_e$, —P(=O)$_2OR_e$, —$U_1$—$NR_bR_c$, —$U_1$—N($R_d$)—$U_2$—$NR_bR_c$, —$U_1$—$NR_d$—$U_2$—$R_b$, —$NR_bP$(=O)$_2R_e$, —P(=O)$_2NR_bR_c$, —C(=O)$OR_e$, —C(=O)$R_a$, —OC(=O)$R_a$, —$NR_dP$(=O)$_2NR_bR_c$, —$R_bP$(=O)$_2R_e$, —$U_1$-aryl, —$U_1$-heteroaryl, —$U_1$-cycloalkyl, —$U_1$-heterocyclo, —$U_1$-arylene-$R_e$, —$U_1$-heteroarylene-$R_e$, —$U_1$-cycloalkylene-$R_e$, and/or —$U_1$-heterocyclene-$R_e$, wherein, in group (i), (ii) —$U_1$— and —$U_2$— are each independently a single bond, —$U^3$—S(O)$_t$—$U^4$—, —$U^3$—C(O)—$U^4$—, —$U^3$—C(S)—$U^4$—, —$U^3$—O—$U^4$—, —$U^3$—S—$U^4$—, —$U^3$—O—C(O)—$U^4$—, —$U^3$—C(O)—O—$U^4$—, or —$U^3$—C(=$NR_g$)—$U^4$—;

wherein, (iii) $U^3$ and $U^4$ are each independently a single bond, alkylene, alkenylene, or alkynylene;

wherein, in group (i), (iv) $R_a$, $R_b$, $R_c$, $R_d$, and $R_e$ are each independently hydrogen, alkyl, alkenyl, alkynyl, cycloalkyl, aryl, heterocyclo, or heteroaryl, each of which is unsubstituted or substituted with one to four groups $R_f$, except $R_e$ is not hydrogen; or $R_b$ and $R_c$ may be taken together to form a 3- to 8-membered saturated or unsaturated ring together with the atoms to which they are attached, which ring is unsubstituted or substituted with one to four groups listed below for $R_f$; or $R_b$ and $R_c$ together with the nitrogen atom to which they are attached may combine to form a group —N=C $R_g R_h$ where $R_g$ and $R_h$ are each independently hydrogen, alkyl, or alkyl substituted with a group $R_f$; and;

wherein, (v) $R_f$ is at each occurrence independently selected from alkyl, halogen, cyano, hydroxy, —O(alkyl), SH, —S(alkyl), amino, alkylamino, haloalkyl, haloalkoxy, or a lower alkyl substituted with one to two of halogen, cyano, hydroxy, —O(alkyl), SH, —S(alkyl), amino, alkylamino, haloalkyl, and/or haloalkoxy, and wherein, (vi) t is 0, 1 or 2.

The term "alkenyl" as used herein by itself or as part of another group refers to straight or branched chain radicals of 2 to 20 carbons, alternatively 2 to 12 carbons, and/or 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. A substituted alkenyl refers to an alkenyl having one or more substituents (for example 1 to 3 substituents, or 1 to 2 substituents), selected from those defined above for substituted alkyl.

The term "alkynyl" as used herein by itself or as part of another group refers to straight or branched chain hydrocarbon groups having 2 to 12 carbon atoms, alternatively 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. A substituted alkynyl refers to an alkynyl having one or more substituents (for example 1 to 4 substituents, or 1 to 2 substituents), selected from those defined above for substituted alkyl.

When the term "alkyl" is used as a suffix with another group, such as in (aryl)alkyl or arylalkyl, this conjunction is meant to refer to a substituted alkyl group wherein at least one of the substituents is the specifically named group in the conjunction. For example, (aryl)alkyl refers to a substituted alkyl group as defined above wherein at least one of the alkyl substituents is an aryl, such as benzyl. However, in groups designated —O(alkyl) and —S(alkyl), it should be understood that the points of attachment in these instances are to the oxygen and sulfur atoms, respectively.

Where alkyl groups as defined are divalent, i.e., with two single bonds for attachment to two other groups, they are termed "alkylene" groups. Similarly, where alkenyl groups as defined above and alkynyl groups as defined above, respectively, are divalent radicals having single bonds for attachment to two other groups, they are termed "alkenylene groups" and "alkynylene groups" respectively. Examples of alkylene, alkenylene and alkynylene groups include:

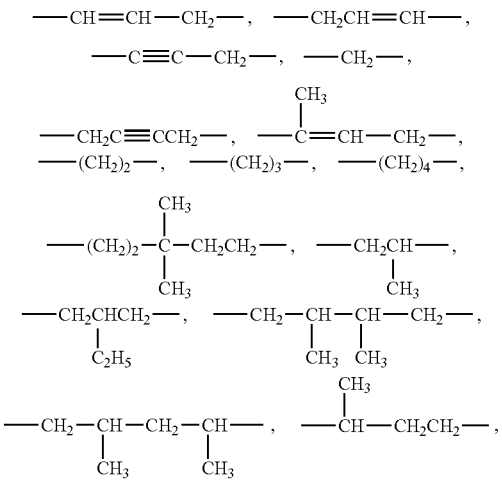

and the like. Alkylene groups may be optionally independently substituted as valence allows with one or more groups as defined for substituted alkyl groups. Thus, for example, a substituted alkylene group would include

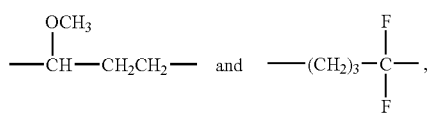

and so forth.

The term "cycloalkyl" as used herein by itself or as part of another group refers to optionally-substituted saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, or 3 to 7 carbons, forming the ring. The further rings of multi-ring cycloalkyls may be either fused, bridged and/or joined through one or more spiro unions. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cycloheptenyl, cyclooctenyl, cyclohexadienyl, cycloheptadienyl,

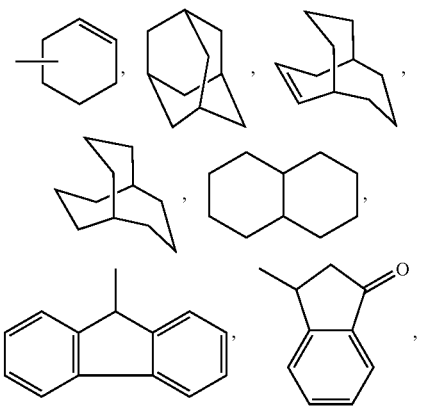

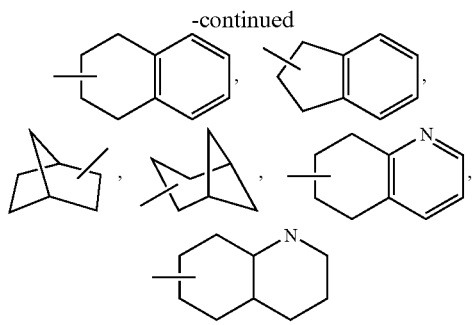

and the like.

Each reference to a cycloalkyl is intended to include both substituted and unsubstituted cycloalkyl groups as defined immediately below, unless reference is made to a particular selection of substituents to be made for the cycloalkyl (e.g., wherein cycloalkyl is substituted with one or more groups $R_f$.) When no particular selection is recited, the optional substituents for the cycloalkyl groups may be selected from the following:

(i) halogen (e.g., a single halo substituent or multiple halo substitutents forming, in the latter case, groups such as a perfluoroalkyl group or an alkyl group bearing $Cl_3$ or $CF_3$), haloalkoxy, cyano, nitro, oxo (=O), —$OR_a$, —$SR_a$, —$S(=O)R_e$, —$S(=O)_2R_e$, —$S(=O)_3H$, —$P(=O)_2$—$R_e$, —$S(=O)_2OR_e$, —$P(=O)_2OR_e$, —$U_1$—$NR_bR_c$, —$U_1$—$N(R_d)$—$U_2$—$NR_bR_c$, —$U_1$—$NR_d$—$U_2$—$R_b$, —$NR_bP(=O)_2R_e$, —$P(=O)_2NR_bR_c$, —$C(=O)OR_e$, —$C(=O)R_a$, —$OC(=O)R_a$, —$NR_dP(=O)_2NR_bR_c$, —$R_bP(=O)_2R_e$, and/or —$U_1$—$R_e$, and/or (ii) —$U_1$-alkyl, —$U_1$-alkenyl, or —$U_1$-alkynyl wherein the alkyl, alkenyl, and alkynyl are substituted with one or more (or 1 to 3) groups recited in (i), wherein, in groups (i) and (ii), (iii) —$U_1$— and —$U_2$— are each independently a single bond, —$U^3$—$S(O)_t$—$U^4$—, —$U^3$—$C(O)$—$U^4$—, —$U^3$—$C(S)$—$U^4$—, —$U^3$—$O$—$U^4$—, —$U^3$—$S$—$U^4$—, —$U^3$—$O$—$C(O)$—$U^4$—, —$U^3$—$C(O)$—$O$—$U^4$—, or —$U^3$—$C(=NR_g)$—$U^4$—;

wherein, in group (iii), (iv) $U^3$ and $U^4$ are each independently a single bond, alkylene, alkenylene, or alkynylene;

wherein, (v) $R_a$, $R_b$, $R_c$, $R_d$, and $R_e$ are each independently hydrogen, alkyl, alkenyl, alkynyl, cycloalkyl, aryl, heterocyclo, or heteroaryl, each of which is unsubstituted or substituted with one or more groups $R_f$, except $R_e$ is not hydrogen; or $R_b$ and $R_c$ may be taken together to form a 3- to 8-membered saturated or unsaturated ring together with the atoms to which they are attached, which ring is unsubstituted or substituted with one or more groups listed below for $R_f$; or $R_b$ and $R_c$ together with the nitrogen atom to which they are attached may combine to form a group —N=C $R_gR_h$, where $R_g$ and $R_h$ are each independently hydrogen, alkyl, or alkyl substituted with a group $R_f$; and;

wherein, (vi) $R_f$ is at each occurrence independently selected from alkyl, halogen, cyano, hydroxy, —O(alkyl), SH, —S(alkyl), amino, alkylamino, haloalkyl, haloalkoxy, or a lower alkyl substituted with one to two of halogen, cyano, hydroxy, —O(alkyl), SH, —S(alkyl), amino, alkylamino, haloalkyl, and/or haloalkoxy, and wherein, (vii) t is 0, 1 or 2.

When the suffix "ene" is used in conjunction with a cyclic group, this is intended to mean the cyclic group as defined herein having two single bonds as points of attachment to other groups. Thus, for example, the term "cycloalkylene" as employed herein refers to a "cycloalkyl" group as defined above which is a linking group such as

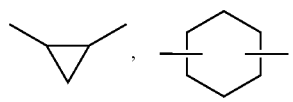

and the like.

The term "alkoxy" refers to an alkyl or substituted alkyl group as defined above bonded through an oxygen atom (—O—), i.e., the group —$OR_i$, wherein $R_i$ is alkyl or substituted alkyl.

The term "alkylthio" refers to an alkyl or substituted alkyl group as defined above bonded through a sulfur atom (—S—), i.e., the group —$SR_i$, wherein $R_i$ is alkyl or substituted alkyl.

The term "acyl" refers to a carbonyl group linked to a radical such as, but not limited to, alkyl, alkenyl, alkynyl, aryl, carbocyclyl, heterocyclyl, more particularly, the group $C(=O)R_j$, wherein $R_j$ can be selected from alkyl, alkenyl, substituted alkyl, or substituted alkenyl, as defined herein.

The term "alkoxycarbonyl" refers to a carboxy group

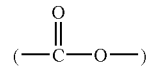

linked to an alkyl radical (i.e., to form $CO_2R_j$), wherein $R_j$ is as defined above for acyl. When the designation "$CO_2$" is used herein, this is intended to refer to the group

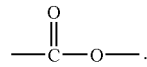

The term "alkylamino" refers to amino groups wherein one or both of the hydrogen atoms is replaced with an alkyl group, i.e., $NR_kR_l$, wherein one of $R_k$ and $R_l$ is hydrogen and the other is alkyl, or both $R_k$ and $R_l$ are alkyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The terms "ar" or "aryl" as used herein by itself or as part of another group refer to optionally-substituted aromatic homocyclic (i.e., hydrocarbon) monocyclic, bicyclic or tricyclic aromatic groups containing 6 to 14 carbons in the ring portion [such as phenyl, biphenyl, naphthyl (including 1-naphthyl and 2-naphthyl) and antracenyl], and may optionally include one to three additional rings (either cycloalkyl, heterocyclo or heteroaryl) fused thereto. Examples include:

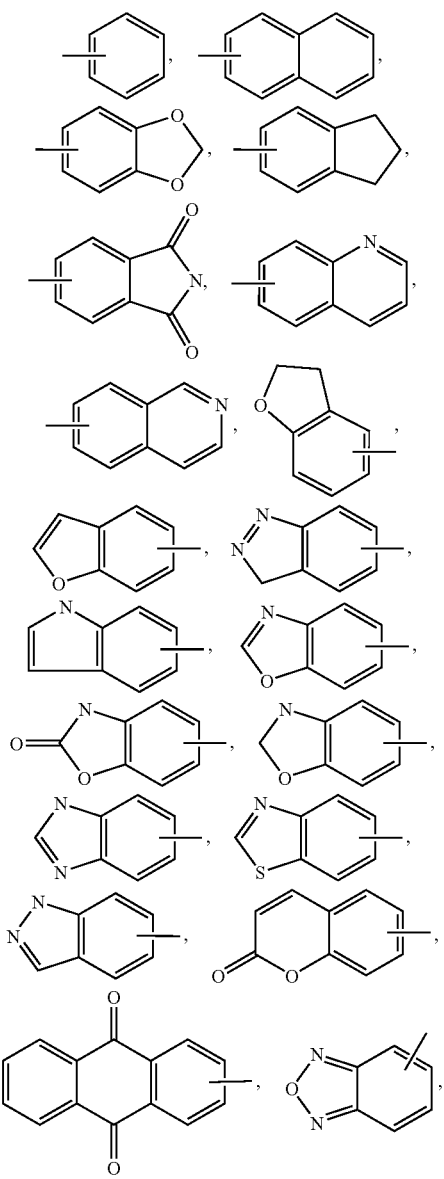

and the like.

Each reference to an aryl is intended to include both substituted and unsubstituted aryl groups as defined herein, unless reference is made to a particular selection of substituents to be made for the aryl (e.g., as when aryl is substituted with one or more groups $R_f$ above). When no particular selection is recited, the optional substituents for the aryl groups may be selected from those recited above, as valence allows, for cycloalkyl groups.

The term "heteroaryl" as used herein by itself or as part of another group refers to optionally-substituted monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

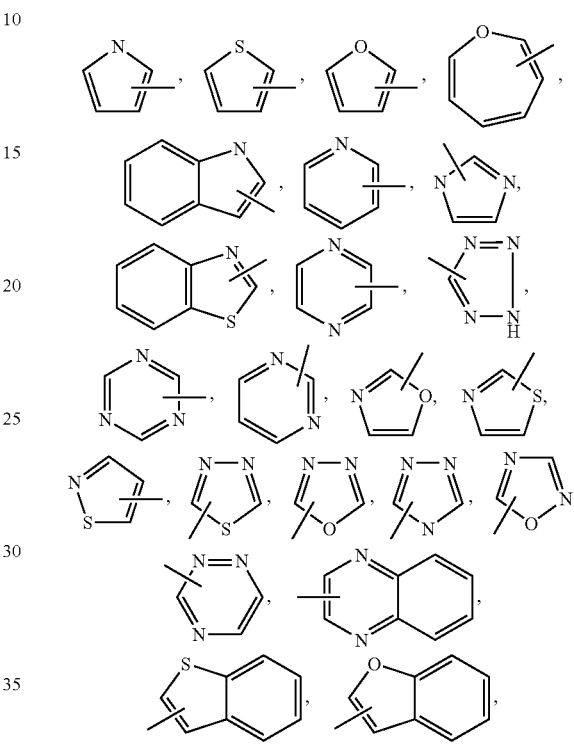

and the like.

Each reference to a heteroaryl is intended to include both substituted and unsubstituted heteroaryl groups as defined herein, unless reference is made to a particular selection of substituents to be made for the heteroaryl (e.g., as when heteroaryl is substituted with one or more groups $R_f$ above). When no particular selection is recited, the optional substituents for the heteroaryl groups may be selected from those recited above, as valence allows, for cycloalkyl groups.

The terms "heterocyclic" or "heterocyclo" as used herein by itself or as part of another group refer to non-aromatic, optionally substituted, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro unions.

Exemplary heterocyclic groups include oxetanyl, imidazolinyl, oxazolidinyl, isoxazolinyl, thiazolidinyl, isothiazolidinyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

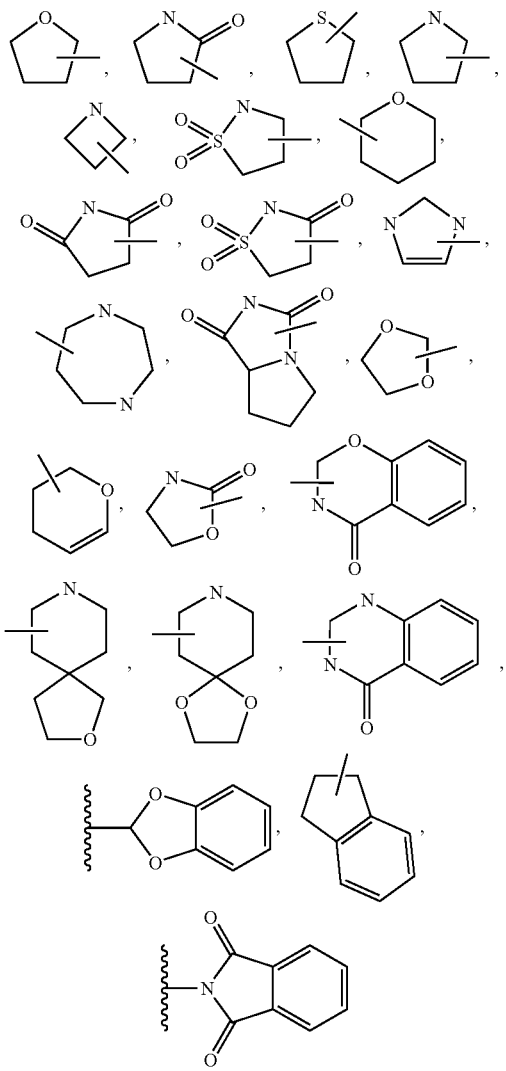

and the like, which optionally may be substituted.

Each reference to a heterocyclo is intended to include both substituted and unsubstituted heterocyclo groups as defined herein, unless reference is made to a particular selection of substituents to be made for the heterocyclo (e.g., as when heterocyclo is substituted with one or more groups $R_6$ above). When no particular selection is recited, the optional substituents for the heterocyclo groups may be selected from those recited above, as valence allows, for cycloalkyl groups.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated, the reference is intended to include rings having 0 to 3, or 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, unless otherwise specified, the ring or group may be fully unsaturated or partially unsaturated.

"Base" when used herein includes metal oxides, hydroxides or alkoxides, hydrides, or compounds such as ammonia, that accept protons in water or solvent. Thus, exemplary bases include, but are not limited to, alkali metal hydroxides and alkoxides (i.e., MOR, wherein M is an alkali metal such as potassium, lithium, or sodium, and R is hydrogen or alkyl, as defined above, or where R is straight or branched chain $C_{1-5}$ alkyl, thus including, without limitation, potassium hydroxide, potassium tert-butoxide, potassium tert-pentoxide, sodium hydroxide, sodium tert-butoxide, lithium hydroxide, etc.); other hydroxides such as magnesium hydroxide (Mg$(OH)_2$) or calcium hydroxide ($Ca(OH)_2$); alkali metal hydrides (i.e., MH, wherein M is as defined above, thus including, without limitation, sodium hydride and lithium hydride); alkylated disilazides, such as, for example, potassium hexamethyldisilazide and lithium hexamethyldisilazide; carbonates such as potassium carbonate ($K_2CO_3$), sodium carbonate ($Na_2CO_3$), potassium bicarbonate ($KHCO_3$), and sodium bicarbonate ($NaHCO_3$), alkyl ammonium hydroxides such as n-tetrabutyl ammonium hydroxide (TBAH); and so forth. The term "coupling reagent" as used herein refers to a reagent used to couple a carboxylic acid and an amine or an aniline to form an amide bond. It may include a coupling additive, such as CDI, HOBt, HOAt, HODhbt, HOSu, or NEPIS, used in combination with another coupling reagent to speed up coupling process and inhibit side reactions. Particular peptide-coupling reagents may include CDI, DCC, EDC, BBC, BDMP, BOMI, HATU, HAPyU, HBTU, TAPipU, AOP, BDP, BOP, PyAOP, PyBOP, TDBTU, TNTU, TPTU, TSTU, BEMT, BOP-Cl, BroP, BTFFH, CIP, EDPBT, Dpp-Cl, EEDQ, FDPP, HOTT-PF6, TOTT-BF4, PyBrop, PyClop, and TFFH. See "Peptide Coupling Reagents: Names, Acronyms and References," Albany Molecular Research, Inc., Technical Reports, Vol. 4, No. 1, incorporated herein by reference.

The terms "halogenating agent" or "halogenating reagent" mean an agent or agents capable of halogenating compounds of formula (II) herein. Halogenating reagents include inorganic and organic halogenating reagents. Examples of inorganic halogenating reagents include chlorine, bromine, iodine, fluorine, and sodium hypochlorite. Organic halogenting reagents include N-chlorosuccinimide (NCS), N-bromosuccinimide (NBS), N-iodosuccinimide (NIS), 1,3-dichloro-5,5-dimethylhydantoin, 1,3-dibromo-5,5-dimethylhydantoin, and 1,3-diiodo-5,5-dimethylhydantoin.

"High yield" as used herein means a yield of greater than 80%, greater than 85%, than 90%, or than 95%.

"Leaving group" means groups having the capability of being displaced upon reaction with a nucleophile including I, Br, Cl, $R_{10}SO_2O$— (wherein $R_{10}$ is alkyl, substituted alkyl, aryl, or heteroaryl, as defined herein), and weak bases, such as, for example, $HSO_4$—. Examples of leaving groups include I, Br, Cl, and ions of methyl sulfate, mesylate (methane sulfonate), trifluromethanesulfonate, and tosylate (p-toluenesulfonate).

In compounds of formula (II) herein, the group Q is —O—P*, wherein P* is selected so that, when considered together with the oxygen atom to which P* is attached, Q is a leaving group, i.e., Q has the capability of being displaced upon reaction with a nucleophile. Accordingly, the group P* may be selected from alkyl, —SO$_2$O R$_{10}$, —SO$_2$R$_{10}$, —C(=O)R$_{11}$ and —Si(R$_{12}$)$_3$, wherein R$_{10}$ is defined as above in the definition of "leaving group," R$_{11}$ is alkyl, aryl or heteroaryl, and R$_{12}$ is selected from alkyl and aryl.

"Suitable solvent" as used herein is intended to refer to a single solvent as well as mixtures of solvents. Solvents may be selected, as appropriate for a given reaction step, from, for example, aprotic polar solvents such as DMF, DMA, DMSO, dimethylpropyleneurea, N-methylpyrrolidone (NMP), and hexamethylphosphoric triamide; ether solvents such as diethyl ether, THF, 1,4-dioxane, methyl t-butyl ether, dimethoxymethane, and ethylene glycol dimethyl ether; alcohol solvents such as MeOH, EtOH, and isopropanol; and halogen-containing solvents such as methylene chloride, chloroform, carbon tetrachloride, and 1,2-dichloroethane. Mixtures of solvents may also include biphasic mixtures.

The term "slurry" as used herein is intended to mean a saturated solution of the compound of Formula (IV) and an additional amount of the compound of Formula (IV) to give a heterogeneous solution of the compound of Formula (IV) and a solvent.

The present invention describes crystalline forms of the compound of formula (IV) in substantially pure form. As used herein, "substantially pure" means a compound having a purity greater than 90 percent, including 90, 91, 92, 93, 94, 95, 96, 97, 98, 99, and 100 percent.

As one example, a crystalline form of the compound of the formula (IV) can be substantially pure in having a purity greater than 90 percent, where the remaining less than 10 percent of material comprises other form(s) of the compound of the formula (IV), and/or reaction and/or processing impurities arising from its preparation. A crystalline form of the compound of the formula (IV) in substantially pure form may therefore be employed in pharmaceutical compositions to which other desired components are added, for example, excipients, carriers, or active chemical entities of different molecular structure.

When dissolved, crystalline forms of the compound of formula (IV) loses its crystalline structure, and is therefore referred to as a solution of the compound of formula (IV). All forms of the present invention, however, may be used for the preparation of liquid formulations in which the drug is dissolved or suspended. In addition, the crystalline forms of the compound of formula (IV) may be incorporated into solid formulations.

A therapeutically effective amount of the crystalline forms of the compound of formula (IV) is combined with a pharmaceutically acceptable carrier to produce the pharmaceutical compositions of this invention. By "therapeutically effective amount" it is meant an amount that, when administered alone or an amount when administered with an additional therapeutic agent, is effective to prevent, suppress or ameliorate the disease or condition or the progression of the disease or condition.

General Methods

This invention is related to a process for the preparation of 2-aminothiazolyl-5-aromatic amides which are useful as inhibitors of kinases, particularly protein tyrosine kinase and p38 kinase. The process involves halogenation of β-(P*)oxy-α,β-unsaturated carboxyl aromatic amides (II) (wherein P* is as defined herein), such as β-(alkyl)oxy-α,β-unsaturated carboxylbenzamides, and reaction with thioureas (III) to give 2-aminothiazole-5-aromatic amides of formula (I). Desired substituents on the 2-amino group and/or the 5-aromatic group can be attached either before or after the aminothiozole formation. For example, in one embodiment, the compound of formula (I) is prepared via reaction of a thiourea wherein R$_4$ is hydrogen, and the R$_4$ hydrogen atom is then elaborated to more functionalized groups such as, in one embodiment, substituted pyrimidines. In another embodiment, the compound of formula (I) is prepared via reaction of a thiourea wherein R$_4$ is a pyrimidinyl, and the pyrimidinyl optionally is further elaborated with additional substituents, as desired.

The process provides an efficient route for preparing 2-aminothiazolyl-5-aromatic amides, essentially in one step and in high yield, without use of expensive coupling reagents or catalysts. Surprisingly, with this process halogenation followed by reaction with thiourea to form the aminothizole is achieved without an undesired aromatic halogenation.

One embodiment of the invention is represented in Scheme 1.

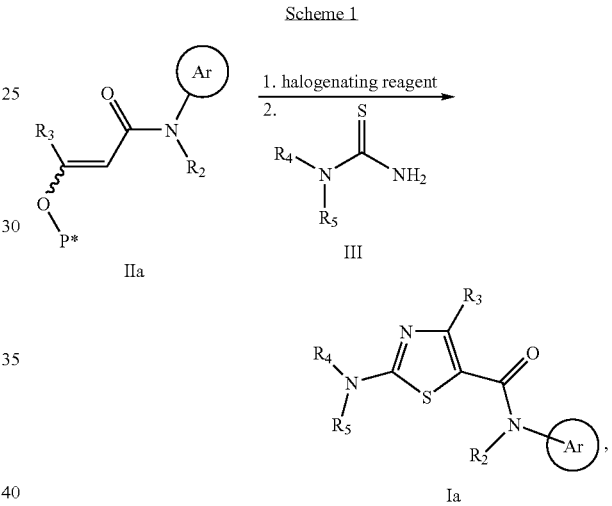

In Scheme 1, Ar is aryl or heteroaryl, more preferably aryl, even more preferably optionally-substituted phenyl. Most preferred is the process involving compounds wherein Ar is phenyl substituted with one to three of alkyl, halogen, —C(=O)NR$_8$, and/or NR$_8$C(=O), wherein R$_8$ is alkyl, cycloalkyl, or heteroaryl, more preferably wherein R$_8$ is cyclopropyl or methyl, and even more preferably wherein Ar is selected from 2-chloro-6-methylphenyl, N-cyclopropyl-1-methyl-benzamide, and N, 1-dimethyl-benzamide. The inventive process may be carried out where a linker group L is present, as in formula I, but advantageously the Ar group is directly attached to the carboxylamide nitrogen atom, as in formula (Ia).

As noted, the desired substituents may be attached to the group Ar either before or after the halogenation and cyclization process. Likewise, the thiourea compounds (III) may be prepared, prior to the cyclization, having desired groups R$_4$ and R$_5$, corresponding to the groups on the desired final product, or alternatively, the desired groups may be attached to the amino-thiazolyl after cyclization. For example, thiourea compounds (III) may be prepared and used in the reaction wherein R$_4$ and R$_5$ are both hydrogen, or R$_4$ and R$_5$ are other groups, different from those of the final desired product, and then, after formation of the aminothiazole (I) or (Ia), the groups $R_4$ and $R_5$ are elaborated to the substituents of the final desired product. All such alternative embodiments and variations thereof are contemplated as within the scope of the present invention.

In intermediates of formula (II) and (IIa), herein, preferably the group P* may be selected from alkyl, —$SO_2OR_{10}$, —$SO_2R_{10}$, —$C(=O)R_{11}$ and —$Si(R_{12})_3$, as defined above, but preferably P* is an alkyl, more preferably a lower alkyl, i.e., methyl, ethyl, n-propyl, isoP, or a straight or branched butyl. Preferably the group $R_2$ is hydrogen or lower alkyl, more preferably hydrogen, and $R_3$ is preferably hydrogen. For compounds (II), β-alkyloxy-α,β-unsaturated carboxylbenzamides are thus preferred, including β-substituted and β-unsubstituted β-alkyloxy-α,β-unsaturated carboxyl benzamides, with the latter more preferred, wherein the phenyl group of the benzamide is optionally substituted as recited above for Ar in formula (Ia). Also preferred β-unsubstituted β-alkyloxy-α,β-unsaturated carboxylbenzamides are β-ethoxy acryl benzamides, again, wherein the phenyl group of the benzamide is optionally substituted as recited above for Ar. Intermediates (II) and (IIa) can be prepared upon reaction of the corresponding anilines, $NHR_2$—Ar, with alkoxyacryloyl compounds. Methods for making β-ethoxy acryl benzamides are also described, for example, in Ashwell, M. A. et al., *J. Bioorg. Med. Chem. Lett.* (2001), 24, at 3123; and Yoshizaki, S., et al. *Chem. Pharm. Bull.* (1980), 28, at 3441, incorporated herein by reference.

The halogenating agent(s) used in the process may be any agent or agents as defined herein capable of halogenating compounds (II), as previously defined herein. Preferred agents include NBS and the N-halohydantoins. Thiourea compounds (III) include unsubstituted thioureas, N-monosubstituted thioureas, and N,N-disubstituted thioureas. The steps of halogenation and cyclization are carried out in a suitable solvent which may include one or more solvents such as hydrocarbons, ethers, esters, amides and ketones with ethers, with dioxane preferred.

Another embodiment of the invention is illustrated in Scheme 2.

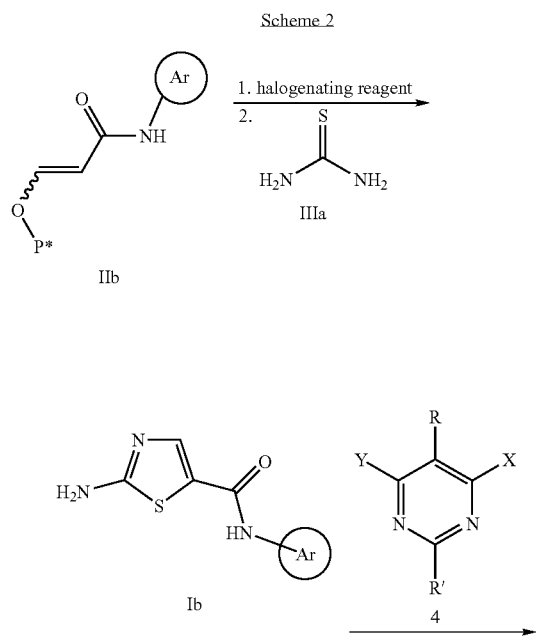

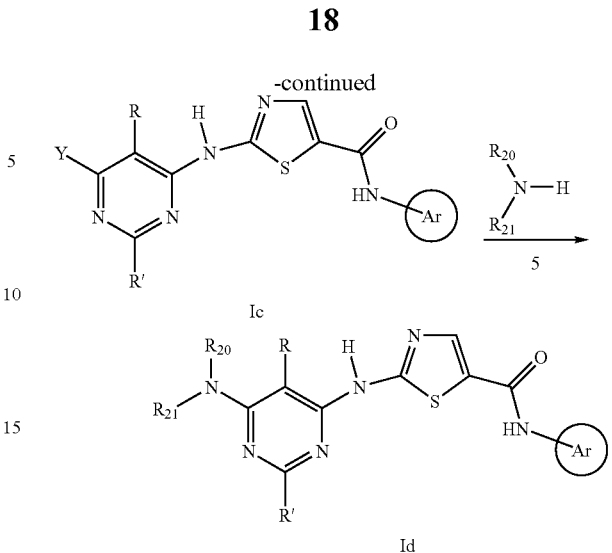

As can be seen, in Scheme 2, the β-(P*)oxy-acryl benzamides (IIb), wherein $R_2$ and $R_3$ are hydrogen, and P* is as previously defined herein, preferably a lower alkyl, are halogenated with a halogenating agent, such as NBS, in a suitable solvent, in the presence of water, then cyclized with unsubstituted thiourea (IIIa). The resulting 2-(unsubstituted) amino-thiazole-5-aromatic amide (Ib) is reacted with a pyrimidine compound 4, wherein R and R' are hydrogen or optional substituents, more preferably hydrogen or lower alkyl, and X and Y are both leaving groups, as defined herein, to produce compounds Ic. Leaving groups X and Y are preferably I, Br, Cl, or $R_{10}SO_2O$— (wherein $R_{10}$ is alkyl, substituted alkyl, aryl, or heteroaryl, as defined herein), more preferably X and Y are selected from I, Br, Cl, methyl sulfate, mesylate, trifluoromethanesulfonate, and tosylate, even more preferably from Cl and Br. Thus, pyrimidines 4 include bishalogen and sulfonyloxy substituted pyrimidines with the former such as bis-chloro substituted pyrimidines preferred. Advantageously, this step is carried out in the presence of a base, wherein the bases may include alkali hydride and alkoxides with the latter such as sodium t-butoxide preferred. Suitable solvent(s) include solvents such as hydrocarbons, ethers, esters, amides, ketones and alcohols, or mixtures of the above solvents, with ether such as THF preferred.

Compound (Ic) can then be reacted with amine $NHR_{20}R_{21}$ (5), to provide compounds of formula (Id). For example, $R_{20}$ and $R_{21}$ can both be hydrogen, or $R_{20}$ and $R_{21}$ can be independently selected from hydrogen, alkyl, substituted alkyl, cycloalkyl, heterocyclo, aryl, and heteroaryl, or $R_{20}$ and $R_{21}$ can be taken together to form a heterocyclo. Preferably, $R_{20}$ and $R_{21}$ are taken together so that $NHR_{20}R_{21}$ forms an optionally-substituted piperazine, more preferably a piperazine N'-substituted with substituted alkyl, more preferably hydroxyethyl. Advantageously, this step is carried out in the presence of a base, including inorganic and organic bases, with organic bases such as tertiary amines preferred. Suitable solvent(s) include solvents such as hydrocarbons, halogenated hydrocarbons, ethers, esters, amides, ketones, lactams and alcohols, and mixtures of the above solvents, with alcohols such as n-butanol as one nonlimiting example, and DMF (dimethylformamide), DMA (dimethylacetamide) and NMP (N-methylpyrrolidine) as other examples. The compounds of formula (Id) thus formed may optionally be further elaborated as desired and/or purified and crystallized.

An alternative approach is illustrated in Scheme 3, wherein a mono-substituted thiourea compound (IIIb) is used.

Scheme 3

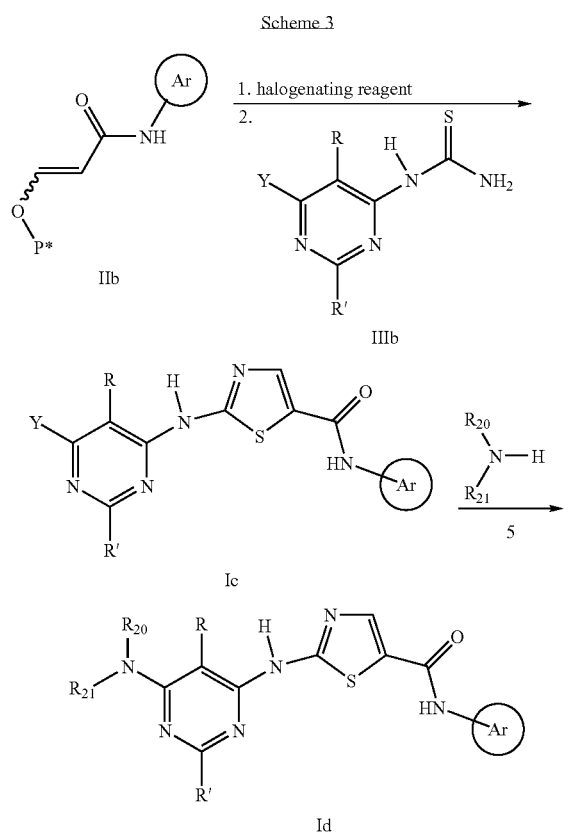

As can be seen, in Scheme 3, the β-(P*)oxy-acryl benzamides (IIb), as in Scheme 2, are halogenated with a halogenating agent, then further reacted with a monosubstituted thiourea (IIIb) having attached thereto a functional pyrimidine group, wherein R, R' and Y are as in Scheme 2, to provide intermediate 2-substituted-aminothiazole-aromatic amides of formula (Ic). The compounds of formula (Ic) may optionally then be reacted with amines NHR$_{20}$R$_{21}$ (5), to provide compounds of formula (Id), and/or optionally further elaborated as desired, and/or purified and crystallized.

FURTHER EMBODIMENTS

In one embodiment, the process comprises preparing a compound of the formula (Ie),

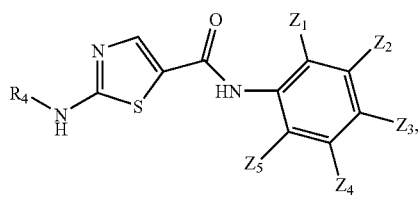

(Ie)

wherein Z$_1$ and Z$_5$ are selected from hydrogen, alkyl, halogen, hydroxy, and alkoxy;

Z$_2$, Z$_3$ and Z$_4$ are selected from hydrogen, alkyl, halogen, hydroxy, alkoxy, C(=O)NR$_8$, and/or NR$_8$C(=O), wherein R$_8$ is alkyl, cycloalkyl, or heteroaryl;

comprising reacting a compound having the formula,

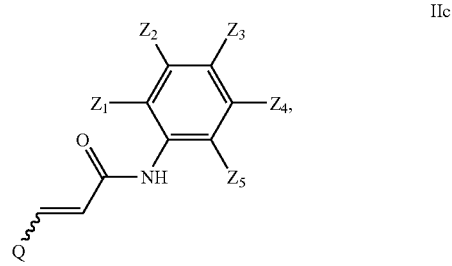

(IIc)

wherein Q is the group —O—P*, wherein P* is selected so that, when considered together with the oxygen atom to which P* is attached, Q is a leaving group, and Z$_1$, Z$_2$, Z$_3$, Z$_4$, and Z$_5$ are as defined above, with a halogenating reagent followed in the presence of water by a thiourea compound having the formula,

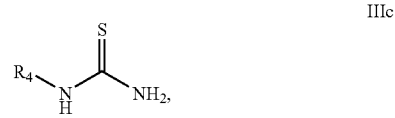

(IIIc)

to provide the compound having the formula (Ie),

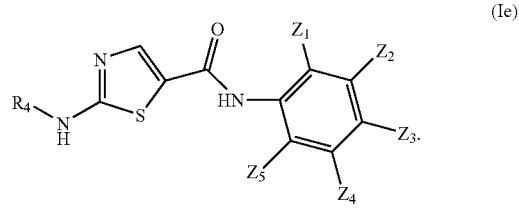

(Ie)

In the above process, in one embodiment, R$_4$ is hydrogen, whereby the process provides a compound having the formula (If),

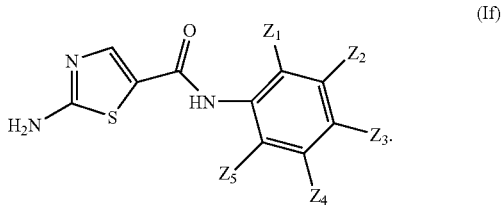

(If)

In another embodiment, R$_4$ may be a group having the formula,

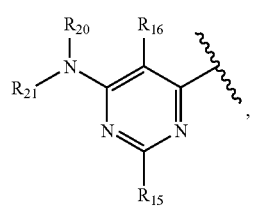

wherein $R_{15}$ and $R_{16}$ are as defined herein, whereby said process provides a compound having the formula (Ih),

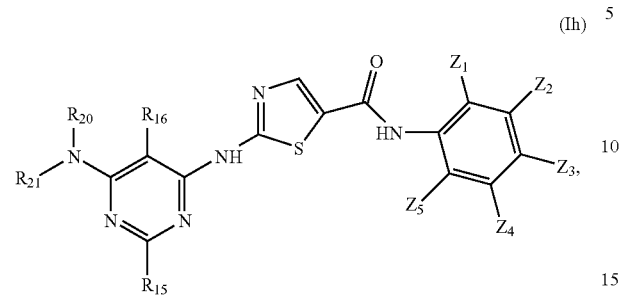

(Ih)

wherein $R_{15}$, $R_{16}$, $Z_1$, $Z_2$, $Z_3$, $Z_4$, $Z_5$, $R_{20}$ and $R_{21}$ are as defined herein.

In yet another embodiment, $R_4$ is a group having the formula,

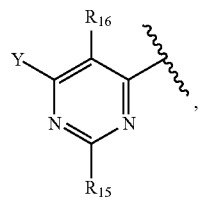

wherein Y, $R_{15}$ and $R_{16}$ are as defined herein, wherein said process provides a compound having the formula (Ii),

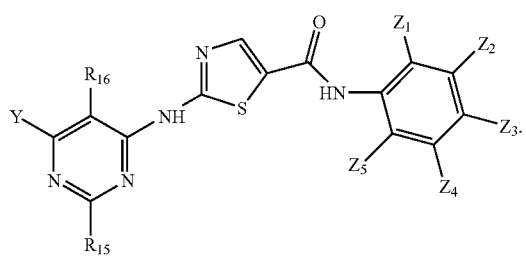

(Ii)

In yet another embodiment, $R_4$ is a group having the formula,

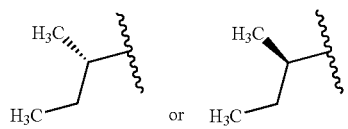

In another embodiment of the above process, e.g., when $R_4$ is hydrogen to provide compounds (If), the process may further comprise reacting the compound of the formula

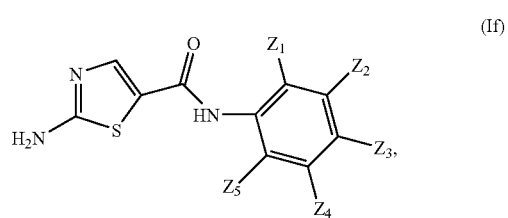

(If)

with a pyrimidine compound having the formula,

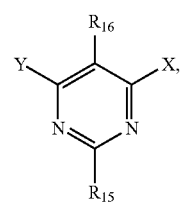

4a wherein X and Y are leaving groups, and $R_{15}$ and $R_{16}$ are independently selected from hydrogen, alkyl and substituted alkyl, to provide a compound having the formula,

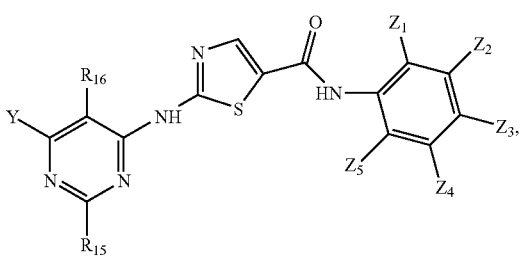

(Ig)

wherein Y, $R_{15}$, $R_{16}$, $Z_1$, $Z_2$, $Z_3$, $Z_4$, and $Z_5$ are as defined above.

In another embodiment of the above process, e.g., when $R_4$ is hydrogen to provide compounds (If), the process may further comprise reacting the compound of the formula

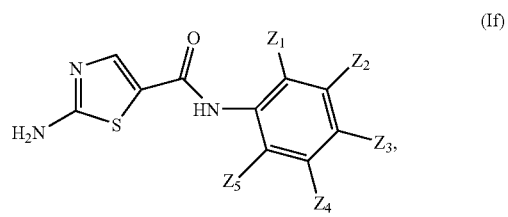

(If)

with a pyrimidine compound having the formula,

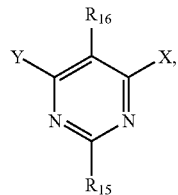

(for example reacting with a base or by metal catalysis)

wherein X and Y are leaving groups, and $R_{15}$ and $R_{16}$ are independently selected from hydrogen, alkyl and substituted alkyl, to provide a compound having the formula,

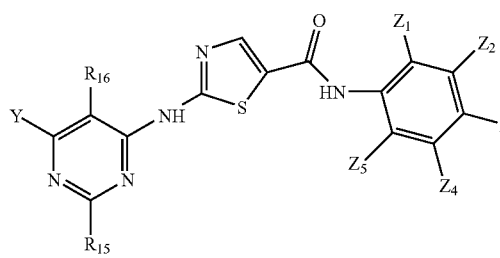

(Ig)

wherein Y, $R_{15}$, $R_{16}$, $Z_1$, $Z_2$, $Z_3$, $Z_4$, and $Z_5$ are as defined above.

Compounds (Ig) may optionally further be reacted with an amine having the formula $NHR_{20}R_{21}$, wherein $R_{20}$ and $R_{21}$ are independently selected from hydrogen, alkyl, substituted alkyl, cycloalkyl, heterocyclo, aryl, and heteroaryl, or $R_{20}$ and $R_{21}$ can be taken together to form a heterocyclo, to provide a compound having the formula (Ih),

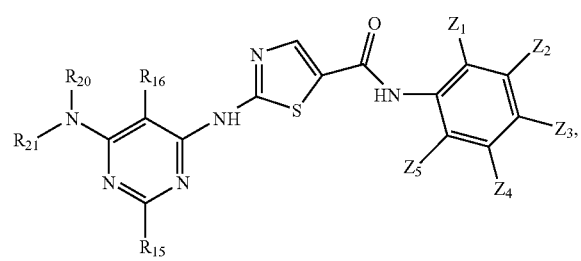

(Ih)

wherein $R_{15}$, $R_{16}$, $Z_1$, $Z_2$, $Z_3$, $Z_4$, $Z_5$, $R_{20}$ and $R_{21}$ are as defined above.

In one embodiment, the amine $NHR_{20}R_{21}$ is piperazine in turn optionally substituted with hydroxy(alkyl), more preferably hydroxyethyl.

In one embodiment, the amine $NHR_{20}R_{21}$ is

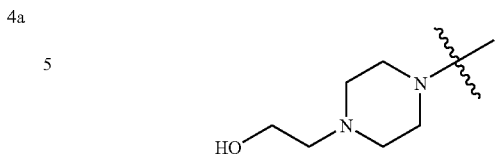

In another embodiment, when $R_4$ is hydrogen to provide compounds (If), the process may further comprise reacting the compound of the formula

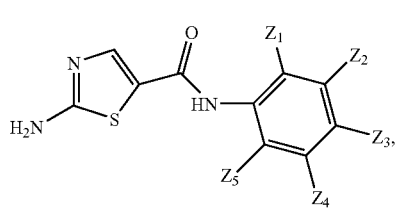

(If)

with a pyrimidine compound having the formula,

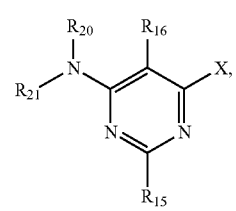

4b wherein $R_{15}$, $R_{16}$, $R_{20}$ and $R_{21}$ are defined as above, to provide a compound having the formula (Ih),

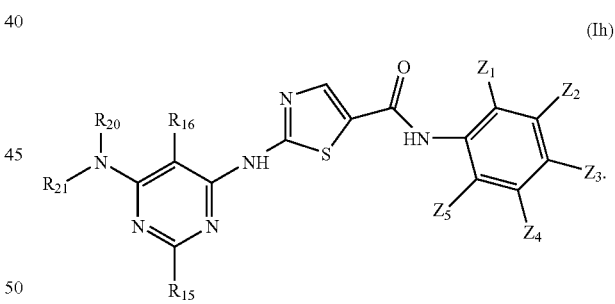

(Ih)

Other variations of the above processes are also contemplated as within the scope of the invention, including processes involving further elaboration of the 2-amino-thiazole-5-aromatic amides.

In one embodiment, the present invention provides a crystalline monohydrate of the compound of formula (IV)

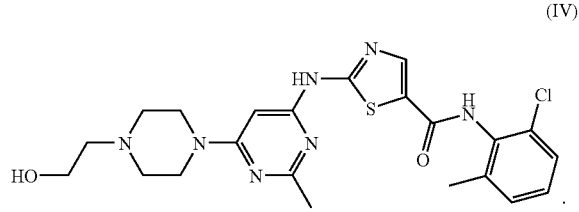

(IV)

In another embodiment, the monohydrate form is in substantially pure form.

In another embodiment, the monohydrate form is in substantially pure form, wherein substantially pure is greater than 90 percent pure.

In another embodiment, the monohydrate form of the compound of Formula (IV) is characterized by an x-ray powder diffraction pattern substantially in accordance with that shown in FIG. 1.

Figure 2:
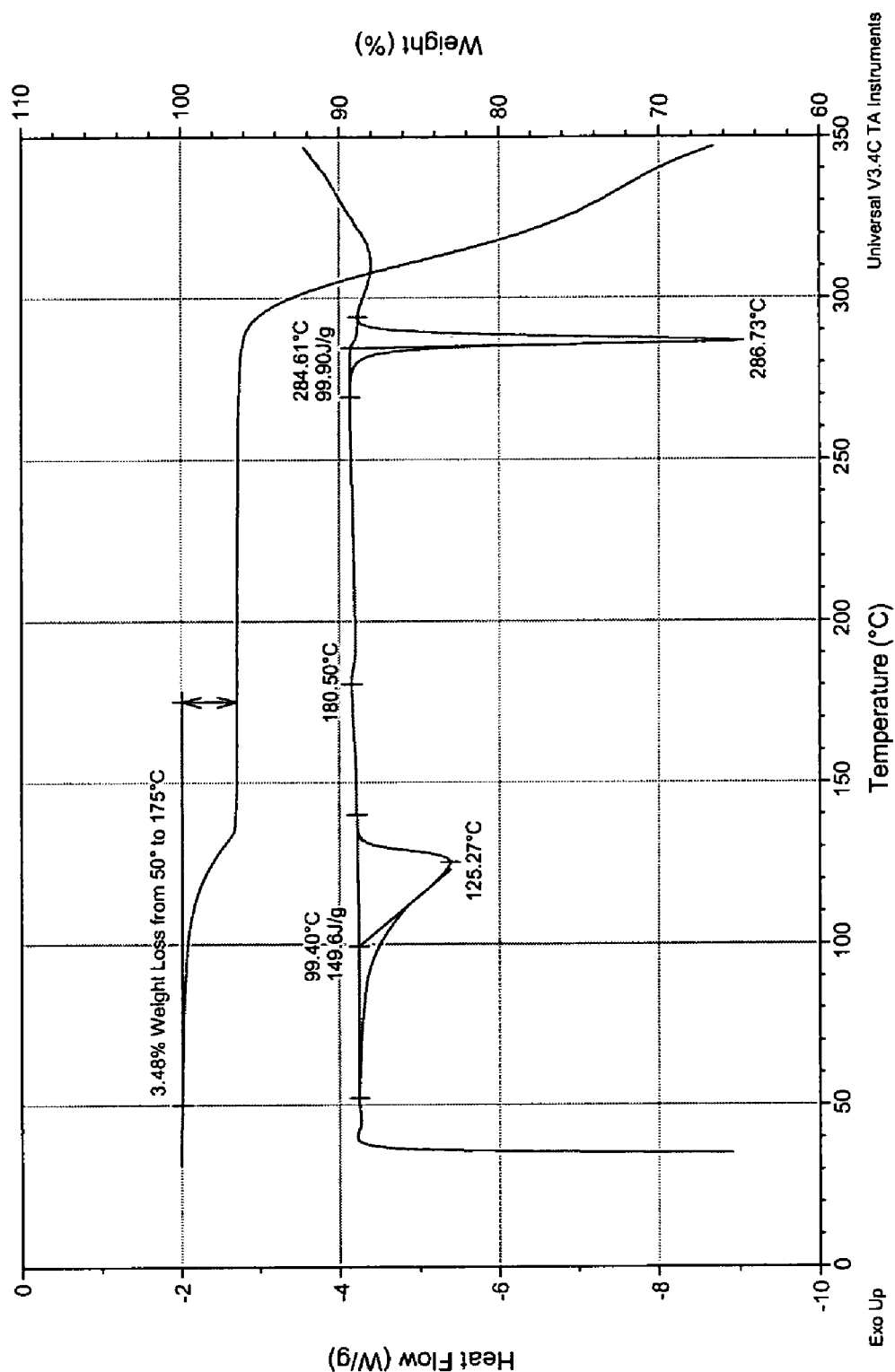
FIG. 2 shows a DSC and TGA of the of the monohydrate crystalline form of the compound of Formula (IV).

In another embodiment, the monohydrate form of the compound of Formula (IV) is characterized by differential scanning calorimetry thermogram and a thermogravimetric anaylsis substantially in accordance with that shown in FIG. 2.

In another embodiment, the monohydrate form of the compound of Formula (IV) is characterized by an x-ray powder diffraction pattern (CuKα λ=1.5418 Å at a temperature of about 23° C.) comprising four or more 2θ values (alternatively, comprising five or more, six or more, or comprising 2θ values) selected from the group consisting of: 18.0±0.2, 18.4±0.2, 19.2±0.2, 19.6±0.2, 21.2±0.2, 24.5±0.2, 25.9±0.2, and 28.0±0.2.

In another embodiment, the monohydrate form of the compound of Formula (IV) is characterized by an x-ray powder diffraction pattern (CuKα λ=1.5418 Å at a temperature of about 23° C.) comprising four or more 2θ values (alternatively, comprising five or more, six or more, or comprising 2θ values) selected from the group consisting of: 4.6±0.2, 11.2±0.2, 13.8±0.2, 15.2±0.2, 17.9±0.2, 19.1±0.2, 19.6±0.2, 23.2±0.2, 23.6±0.2.

In another embodiment, the monohydrate form of the compound of Formula (IV) is characterized by unit cell parameters approximately equal to the following:
Cell dimensions:
a(Å)=13.862(1);
b(Å)=9.286(1);
c(Å)=38.143(2);
Volume=4910(1) Å$^3$
Space group Pbca
Molecules/unit cell 8
Density (calculated) (g/cm$^3$) 1.369 wherein the compound is at a temperature of about −50° C.

In another embodiment, the monohydrate form of the compound of Formula (IV) there is one water molecule per molecule of formula (IV).

In another embodiment, the present invention provides a crystalline butanol solvate of the compound of formula (IV)

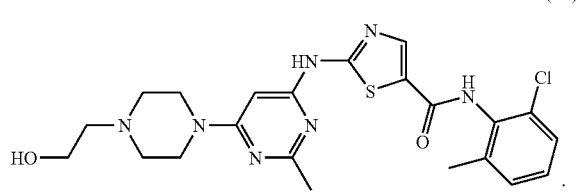

(IV)

In another embodiment, the butanol solvate form of the compound of Formula (IV) is characterized by unit cell parameters approximately equal to the following:
Cell dimensions:
a(Å)=22.8102(6);
b(Å)=8.4691(3);
c(Å)=15.1436(5);
β=95.794(2);
Volume=2910.5(2) Å$^3$
Space group P2$_1$/a
Molecules/unit cell 4
Density (calculated) (g/cm$^3$) 1.283.

In another embodiment, the crystalline butanol solvate of the compound of Formula (IV) is characterized by an x-ray powder diffraction pattern (CuKα λ=1.5418 Å at a temperature of about 23° C.) comprising four or more 2θ values (alternatively, comprising five or more, six or more, or comprising 2θ values) selected from the group consisting of: 5.9±0.2, 12.0±0.2, 13.0±0.2, 17.7±0.2, 24.1±0.2, and 24.6±0.2.

In another embodiment, the present invention is directed to the crystalline ethanol solvate of the compound of formula (IV).

In another embodiment, the crystalline ethanol solvate of the compound of Formula (IV) is characterized by an x-ray powder diffraction pattern (CuKα λ=1.5418 Å at a temperature of about 23° C.) comprising four or more 2θ values (alternatively, comprising five or more, six or more, or comprising 2θ values) selected from the group consisting of: 5.8±0.2, 11.3±0.2, 15.8±0.2, 17.2±0.2, 19.5±0.2, 24.1±0.2, 25.3±0.2, and 26.2±0.2.

In another embodiment, the present invention is directed to the crystalline neat form of the compound of formula (IV).

In another embodiment, the crystalline neat form of the compound of Formula (IV) is characterized by an x-ray powder diffraction pattern (CuKα λ=1.5418 Å at a temperature of about 23° C.) comprising four or more 2θ values (alternatively, comprising five or more, six or more, or comprising 2θ values) selected from the group consisting of: 6.8±0.2, 11.1±0.2, 12.3±0.2, 13.2±0.2, 13.7±0.2, 16.7±0.2, 21.0±0.2, 24.3±0.2, and 24.8±0.2.

In another embodiment, the present invention describes a pharmaceutical composition comprising a therapeutically effective amount of at least one of the crystalline forms of the compound of Formula (IV) and a pharmaceutically acceptable carrier.

In another embodiment, the present invention describes a method for the treatment of cancer which comprises administering to a host in need of such treatment a therapeutically effective amount of at least one of the crystalline forms of the compound of Formula (IV).

In another embodiment, the present invention describes a method of treating oncological disorders which comprises administering to a host in need of such treatment a therapeutically effective amount of at least one of the crystalline forms of the compound of Formula (IV), wherein the disorders are selected from chronic myelogenous leukemia (CML), gastrointestinal stromal tumor (GIST), small cell lung cancer (SCLC), non-small cell lung cancer (NSCLC), ovarian cancer, melanoma, mastocytosis, germ cell tumors, acute myelogenous leukemia (AML), pediatric sarcomas, breast cancer, colorectal cancer, pancreatic cancer, and prostate cancer.

In another embodiment, the present invention is directed to a use of at least one of the crystalline forms of the compound of Formula (IV), in the preparation of a medicament for the treatment of oncological disorders, such as those described herein.

In another embodiment, the present invention is directed to a method of treating of oncological disorders, as described herein, which are resistant or intolerant to Gleevec® (STI-571), comprising administering to a host in need of such treatment a therapeutically effective amount of the compound of Formula (IV) or at least one of the crystalline forms of the compound of Formula (IV).

This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

Utility

The compounds of formula (I) prepared according to the inventive process herein inhibit protein tyrosine kinases, especially Src-family kinases such as Lck, Fyn, Lyn, Src, Yes, Hck, Fgr and Blk, and are thus useful in the treatment, including prevention and therapy, of protein tyrosine kinase-associated disorders such as immunologic and oncologic disorders. The compounds of formula (I) also may inhibit receptor tyrosine kinases including HER1 and HER2 and therefore be useful in the treatment of proliferative disorders such as psoriasis and cancer. The ability of these compounds to inhibit HER1 and other receptor kinases will permit their use as anti-angiogenic agents to treat disorders such as cancer and diabetic retinopathy. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred use for compounds of formula (I) prepared according to the process herein.

Use of the compounds of formula (I) in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; chronic obstructive pulmonary disease (COPD), such as emphysema; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including cancers where Lck or other Src-family kinases such as Src are activated or overexpressed, such as colon carcinoma and thymoma, and cancers where Src-family kinase activity facilitates tumor growth or survival; glomerulonephritis; serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea.

The compounds of the present invention are useful for the treatment of cancers such as chronic myelogenous leukemia (CML), gastrointestinal stromal tumor (GIST), small cell lung cancer (SCLC), non-small cell lung cancer (NSCLC), ovarian cancer, melanoma, mastocytosis, germ cell tumors, acute myelogenous leukemia (AML), pediatric sarcomas, breast cancer, colorectal cancer, pancreatic cancer, prostate cancer and others known to be associated with protein tyrosine kinases such as, for example, SRC, BCR-ABL and c-KIT. The compounds of the present invention are also useful in the treatment of cancers that are sensitive to and resistant to chemotherapeutic agents that target BCR-ABL and c-KIT, such as, for example, Gleevec® (STI-571). In one embodiment of the invention, for example, the compound of the formula (IV) (including, but not limited to the crystalline forms of that compound described herein, such as the crystalline monohydrate) is useful in the treatment of patients resistant or intolerant to Gleevec® (STI-571) of AMN-107 for diseases such as chronic myelogenous leukemias (CML), or other cancers (including other leukemias) as described herein.

In another embodiment of the invention a compound of Formulas I is administered in conjunction with at least one anti-neoplastic agent.

As used herein, the phrase "anti-neoplastic agent" or "anti-cancer agent" is synonymous with "chemotherapeutic agent" and/or "anti-proliferative agent" and refers to compounds that prevent cancer, or hyperproliferative cells from multiplying. Anti-proliferative agents prevent cancer cells from multiplying by: (1) interfering with the cell's ability to replicate DNA and (2) inducing cell death and/or apoptosis in the cancer cells.

Classes of compounds that may be used as anti-proliferative cytotoxic agents and/or anti-proliferative agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (Cytoxan@), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide.

Other anti-proliferative cytotoxic agents and/or anti-proliferative agents are navelbene, CPT-11, anastrazole, letrazole, capecitabine, reloxafine, cyclophosphamide, ifosamide, and droloxafine.

The phrase "radiation therapy" includes, but is not limited to, x-rays or gamma rays which are delivered from either an externally applied source such as a beam or by implantation of small radioactive sources. Radiation therapy may be useful in combination with compounds of the present invention.

The following may also be useful when administered in combination with compounds of the present invention.

Microtubule affecting agents interfere with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E), 7R*,10S*,11R*,12R*,16S*]]-7-11-dihydroxy-8,8,10,12, 16-pentamethyl-3-[1-methyl-2-(2-methyl-4-thiazolyl) ethenyl]-4-aza-17 oxabicyclo [14.1.0]heptadecane-5,9-dione (disclosed in U.S. Pat. No. 6,262,094, issued Jul. 17, 2001), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Ser. No. 09/506,481 filed on Feb. 17, 2000, and examples 7 and 8 herein), [1S1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17oxabicyclo[14.1.0]-heptadecane-5,9-dione, [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione, and derivatives thereof; and other microtubule-disruptor agents. Additional antineoplastic agents include, discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem 271:29807-29812.

In cases where it is desirable to render aberrantly proliferative cells quiescent in conjunction with or prior to treatment with the chemotherapeutic methods of the invention, hormones and steroids (including synthetic analogs): 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, hlorotrianisene, Hydroxyprogesterone, Aminoglutethimide, Estramustine, Medroxyprogesteroneacetate, Leuprolide, Flutamide, Toremifene, Zoladex can also be administered to the patient.

Also suitable for use in the combination chemotherapeutic methods of the invention are antiangiogenics such as matrix metalloproteinase inhibitors, and other VEGF inhibitors, such as anti-VEGF antibodies and small molecules such as ZD6474 and SU6668 are also included. Anti- Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is Casodex™ which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

As mentioned, certain anti-proliferative agents are anti-angiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particular class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors.

Also suitable are anthracyclines (e.g., daunorubicin, doxorubicin), cytarabine (ara-C; Cytosar-U®); 6-thioguanine (Tabloid®), mitoxantrone (Novantrone®) and etoposide (Vepesid®), amsacrine (AMSA), and all-trans retinoic acid (ATRA).

The compounds of the present invention may be useful in combination with BCR-ABL inhibitors such as, but not limited to, Gleevec® (imatinib, STI-571) or AMN-107, the compound shown below

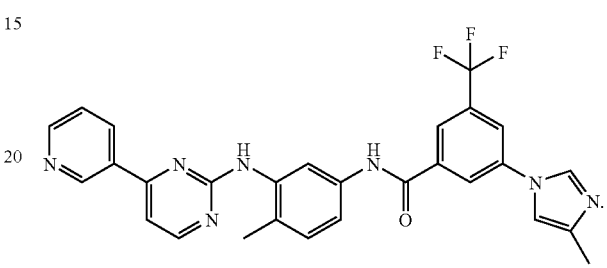

The compounds of the present invention may be useful in combination with anti-cancer compounds such as fentanyl, doxorubicin, interferon alfa-n3, palonosetron dolasetron anastrozole, exemestane, bevacizumab, bicalutamide, cisplatin, dacarbazine, cytarabine, clonidine, epirubicin, levamisole, toremifene, fulvestrant, letrozole, tamsulosin, gallium nitrate, trastuzumab, altretamine, hydroxycarbamide, ifosfamide, interferon alfacon-1, gefitinib, granisetron, leuprorelin, dronabinol, megestrol, pethidine, promethazine, morphine, vinorelbine, pegfilgrastim, filgrastim, nilutamide, thiethylperazine, leuprorelin, pegaspargase, muromonab-CD3, porfimer sodium, cisplatin, abarelix, capromab, samarium SM153 lexidronam, paclitaxel, docetaxel, etoposide, triptorelin, valrubicin, nofetumomab merpentan technetium 99m Tc, vincristine, capecitabine, strptozocin, and ondansetron.

Thus, the present invention provides methods for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

The present invention provides methods for the treatment of a variety of non-cancerous proliferative diseases.

The invention is useful to treat GIST, breast cancer, pancreatic cancer, colon cancer, NSCLC, CML, and ALL, sarcoma, and various pediatric cancers.

The compounds of the present invention are protein tyrosine kinase inhibitors and as such are useful in the treatment of immunological disorders in addition to oncological disorders. U.S. Pat. No. 6,596,746 describes the utility of the compound in immunological disorders and is hereby incorporated by reference for the description of the compound in such immunological disorders.

The present invention also encompasses a pharmaceutical composition useful in the treatment of cancer, comprising the administration of a therapeutically effective amount of the combinations of this invention, with or without pharmaceutically acceptable carriers or diluents. The pharmaceutical compositions of this invention comprise an anti-proliferative agent or agents, a formula I compound, and a pharmaceutically acceptable carrier. The methods entail the use of a neoplastic agent in combination with a Formula I compound. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, Formula I, compounds and compositions of the present invention may be administered orally or parenterally including the intravenous, intramuscular, intraperitoneal, subcutaneous, rectal and topical routes of administration.

The present invention also provides using the compounds obtained with the inventive process to further prepare pharmaceutical compositions capable of treating Src-kinase associated conditions, including the conditions described above. The said compositions may contain other therapeutic agents. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The said pharmaceutical compositions may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds of formula (I) may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds of formula (I), prepared according to the inventive process, may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

An example of a composition for oral administration is the compound of formula (IV), lactose monohydrate(intragranular phase), microcrystalline cellulose(intra-granular phase), croscarmellose sodium(intra-granular phase), hydroxypropyl cellulose(intra-granular phase), microcrystalline cellulose(extra-granular phase), croscarmellose sodium (extra-granular phase), and magnesium stearate(extragranular phase).

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of formula (I) may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Src kinase levels.

When administered intravenously, the compounds of the present invention, including the crystalline forms of the compounds of formula IV, are administered using the formulations of the invention. In one embodiment, the compounds of the present invention, are administered by IV infusion over a period of from about 10 minutes to about 3 hours, preferably about 30 minutes to about 2 hours, more preferably about 45 minutes to 90 minutes, and most preferably about 1 hour. Typically, the compounds are administered intravenously in a dose of from about 0.5 mg/m$^2$ to 65 mg/m$^2$, preferably about 1 mg/m$^2$ to 50 mg/m$^2$, more preferably about 2.5 mg/m$^2$ to 30 mg/m$^2$, and most preferably about 25 mg/m$^2$.

One of ordinary skill in the art would readily know how to convert doses from mg/kg to mg/m$^2$ given either or both the height and or weight of the patient (See, e.g., http://www.fda.gov/cder/cancer/animalframe.htm).

As discussed above, compounds of the present invention, including the crystalline forms of the compounds of formula IV can be administered orally, intravenously, or both. In particular, the methods of the invention encompass dosing protocols such as once a day for 2 to 10 days, preferably every 3 to 9 days, more preferably every 4 to 8 days and most preferably every 5 days. In one embodiment there is a period of 3 days to 5 weeks, alternatively 4 days to 4 weeks, or 5 days to 3 weeks, or 1 week to 2 weeks, in between cycles where there is no treatment. In another embodiment the compounds of the present invention, including the crystalline forms of the compounds of formula IV can be administered orally, intravenously, or both, once a day for 3 days, with a period of 1 week to 3 weeks in between cycles where there is no treatment. In yet another embodiment the compounds of the present invention, the crystalline forms of the compounds of formula IV, can be administered orally, intravenously, or both, once a day for 5 days, with a period of 1 week to 3 weeks in between cycles where there is no treatment.

In another embodiment the treatment cycle for administration of the compounds of the present invention, the crystalline forms of the compounds of formula IV, is once daily for 5 consecutive days and the period between treatment cycles is from 2 to 10 days, or alternatively one week. In one embodiment, a compound of the present invention, for example, a compound of formula IV, is administered once daily for 5 consecutive days, followed by 2 days when there is no treatment.

The compounds of the present invention, the crystalline forms of the compounds of formula IV, can also be administered orally, intravenously, or both once every 1 to 10 weeks, every 2 to 8 weeks, every 3 to 6 weeks, alternatively every 3 weeks.

In another method of the invention, the compounds of the present invention, the crystalline forms of the compounds of formula IV, are administered in a 28 day cycle wherein the compounds are intravenously administered on days 1, 7, and 14 and orally administered on day 21. Alternatively, the compounds of the present invention, the crystalline forms of the compounds of formula IV, are administered in a 28 day cycle wherein the compound of formulae IV are orally administered on day 1 and intravenously administered on days 7, 14, and 28.

In another embodiment of the invention, the compound of formula IV may be administered in a dose of 15-200 mg twice a day, or 30-100 mg twice a day. In one embodiment, the compound of formula IV may be administered at 70 mg twice a day. In another embodiment, the compound of formula IV may be administered in a dose of 50-300 mg once a day, or 100-200 mg once a day. Alternatively, the compound of formula IV may be administered in a dose of 75-150 mg twice a day or 140-250 mg once a day. Alternatively, the compound of formula IV may be administered at 50, 60, 70, 80, 90, 100, 110, 120, 130 or 140 mg twice a day, or doses in between. Alternatively, the compound of formula IV may be administered at 100, 120, 140, 160, 180, 200, 220 or 240 mg once a day, or doses in between. The compound of formula IV may be administered either continuously or on an alternating schedule, such as 5 days on, 2 days off, or some other schedule as described above.

According to the methods of the invention, the compounds of the present invention, including compounds of formulae IV, are administered until the patient shows a response, for example, a reduction in tumor size, or until dose limiting toxicity is reached.

Compounds within the scope of formula (I) may be tested for activity as inhibitors of protein kinases using the assays described below, or variations thereof that are within the level ordinary skill in the art.

Cell Assays (1) Cellular Tyrosine Phosphorylation

Jurkat T cells are incubated with the test compound and then stimulated by the addition of antibody to CD3 (monoclonal antibody G19-4). Cells are lysed after 4 minutes or at another desired time by the addition of a lysis buffer containing NP-40 detergent. Phosphorylation of proteins is detected by anti-phosphotyrosine immunoblotting. Detection of phosphorylation of specific proteins of interest such as ZAP-70 is detected by immunoprecipitation with anti-ZAP-70 antibody followed by anti-phosphotyrosine immunoblotting. Such procedures are described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718-20726 (1994), and the references incorporated therein. The Lck inhibitors inhibit the tyrosine phosphorylation of cellular proteins induced by anti-CD3 antibodies.

For the preparation of G19-4, see Hansen, J. A., Martin, P. J., Beatty, P. G., Clark, E. A., and Ledbetter, J. A., "Human T lymphocyte cell surface molecules defined by the workshop monoclonal antibodies," in *Leukocyte Typing I*, A. Bernard, J. Boumsell, J. Dausett, C. Milstein, and S. Schlossman, eds. (New York: Springer Verlag), p. 195-212 (1984); and Ledbetter, J. A., June, C. H., Rabinovitch, P. S., Grossman, A., Tsu, T. T., and Imboden, J. B., "Signal transduction through CD4 receptors: stimulatory vs. inhibitory activity is regulated by CD4 proximity to the CD3/T cell receptor", *Eur. J. Immunol.*, 18, 525 (1988).

(2) Calcium Assay

Lck inhibitors block calcium mobilization in T cells stimulated with anti-CD3 antibodies. Cells are loaded with the calcium indicator dye indo-1, treated with anti-CD3 antibody such as the monoclonal antibody G19-4, and calcium mobilization is measured using flow cytometry by recording changes in the blue/violet indo-1 ratio as described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718-20726 (1994), and the references incorporated therein.

(3) Proliferation Assays

Lck inhibitors inhibit the proliferation of normal human peripheral blood T cells stimulated to grow with anti-CD3 plus anti-CD28 antibodies. A 96 well plate is coated with a monoclonal antibody to CD3 (such as G19-4), the antibody is allowed to bind, and then the plate is washed. The antibody bound to the plate serves to stimulate the cells. Normal human peripheral blood T cells are added to the wells along with test compound plus anti-CD28 antibody to provide co-stimulation. After a desired period of time (e.g., 3 days), the [3H]-thymidine is added to the cells, and after further incubation to allow incorporation of the label into newly synthesized DNA, the cells are harvested and counted in a scintillation counter to measure cell proliferation.

The following examples illustrate the invention but should not be interpreted as a limitation thereon.

EXAMPLES

Example 1

Preparation of Intermediate:

(S)-1-sec-Butylthiourea

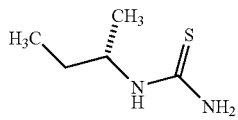

To a solution of S— sec-butyl-amine (7.31 g, 0.1 mol) in chloroform (80 mL) at 0° C. was slowly added benzoyl isothiocyanate (13.44 mL, 0.1 mol). The mixture was allowed to warm to 10° C. and stirred for 10 min. The solvent was then removed under reduced pressure, and the residue was dissolved in MeOH (80 mL). An aqueous solution (10 mL) of NaOH (4 g, 0.1 mol) was added to this solution, and the mixture was stirred at 60° C. for another 2 h. The MeOH was then removed under reduced pressure, and the residue was stirred in water (50 mL). The precipitate was collected by vacuum filtration and dried to provide S-1-sec-butyl-thiourea (12.2 g, 92% yield). mp 133-134° C.; $^1$H NMR (500 MHz, DMSO-D$_6$) δ 7.40 (s, 1H), 7.20 (br s, 1H), 6.76 (s, 1H), 4.04 (s, 1H), 1.41 (m, 2H), 1.03 (d, J=6.1 Hz, 3H), 0.81 (d, J=7.7 Hz, 3H); $^{13}$C NMR (125 MHz, DMSO-D$_6$) δ 182.5, 50.8, 28.8, 19.9, 10.3; LRMS m/z 133.2 (M+H); Anal. Calcd for C$_5$H$_{12}$N$_2$S: C, 45.41; H, 9.14; N, 21.18; S, 24.25. Found: C, 45.49; H, 8.88; N, 21.32; S, 24.27.

Example 2

Preparation of Intermediate:

(R)-1-sec-Butylthiourea

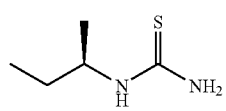

(R)-1-sec-Butylthiourea was prepared in 92% yield according to the general method outlined for Example 1. mp 133-134° C.; $^1$H NMR(500 MHz, DMSO) δ 0.80(m, 3H, J=7.7), 1.02(d, 3H, J=6.1), 1.41(m, 2H), (3.40, 4.04)(s, 1H), 6.76(s, 1H), 7.20(s, br, 1H), 7.39(d, 1H, J=7.2); $^{13}$C NMR (500 MHz, DMSO) δ: 10.00, 19.56, 28.50, 50.20, 182.00; m/z 133.23 (M+H); Anal. Calcd for C$_5$H$_{12}$N$_2$S: C, 45.41; H, 9.14; N, 21.18; S, 24.25. Found: C, 45.32; H, 9.15; N, 21.14; S, 24.38.

Example 3

Preparation of:

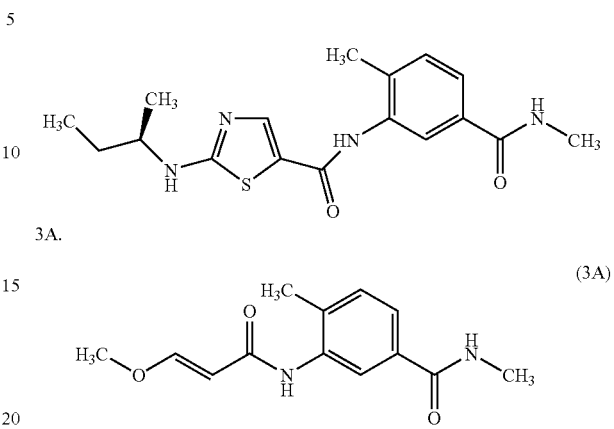

3A.

To a solution of 3-amino-N-methyl-4-methylbenzamide hydrochloride (1.0 g, 5 mmol) in acetone (10 mL) at 0° C. was added pyridine (1.2 mL, 15 mmol) dropwise via syringe. 3-Methoxyacryloyl chloride (0.72 mL. 6.5 mmol) was added and the reaction stirred at room temperature for 1 h. The solution was cooled again to 0° C. and 1N HCl (1.5 mL) was added dropwise via pipet. The reaction mixture was stirred for 5 min, then water (8.5 mL) was added via an addition funnel. The acetone was removed in vacuo and the resulting solution stirred for 4h. Crystallization began within 15 min. After stirring for 4 h, the vessel was cooled in an ice bath for 30 min, filtered, and rinsed with ice cold water (2×3 mL) to give compound 3A (0.99 g, 78% yield) as a white solid. $^1$H NMR (400 MHz, CDCl$_3$) δ 8.95 (s, 1H), 8.12 (br s, 1H), 7.76 (s, 1H), 7.29 (m, 2H), 7.05 (d, J=7.9 Hz, 1H), 5.47 (d, J=12.3 Hz, 1H), 3.48 (s, 3H), 2.54 (d, J=4.7 Hz, 3H), 2.03 (s, 3H); HPLC rt 2.28 min (Condition A).

3B. Example 3

To a 50 mL RBF containing the above compound 3A (0.5 g, 2.0 mmol) was added THF (2.5 mL) and water (2 mL), followed by NBS (0.40 g, 2.22 mmol), and the solution was stirred for 90 min. R-sec-butylthiourea (Ex. 2) (267 mg), was added, and the solution was heated to 75° C. for 8 h. Conc. NH$_4$OH was added to adjust the pH to 10 followed by the addition of EtOH (15 mL). Water (15 mL) was added and the slurry stirred for 16 h, filtered, and washed with water to give Example 3 as a light brown solid (0.48 g, 69% yield, 98% purity). MS 347.1; HPLC 2.59.

Example 4

Preparation of:

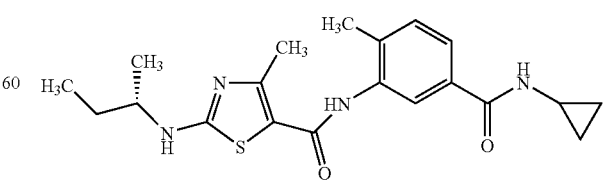

Example 4 is prepared following the methods of Example 3 but using the appropriate acryl benzamide and Example 1.

Example 5

Preparation of:

N-(2-chloro-6-methylphenyl)-2-(6-(4-(3-hydroxy-ethyl)piperazin-1-yl)-2-methylpyrimidin-4-ylamino)thiazole-5-carboxamide (The Compound of Formula (IV))

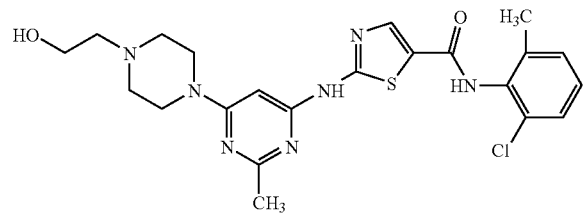

(IV)

5A. 1-(6-Chloro-2-methylpyrimidin-4-yl)thiourea

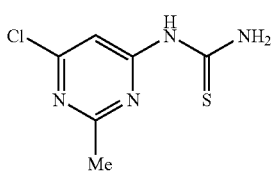

(5A)

To a stirring slurry of 4-amino-5-chloro-2-methylpyrimidine (6.13 g, 42.7 mmol) in THF (24 mL) was added ethyl isothiocyanatoformate (7.5 mL, 63.6 mmol), and the mixture heated to reflux. After 5h, another portion of ethyl isothiocyanato formate (1.0 mL, 8.5 mmol) was added and after 10h, a final portion (1.5 mL, 12.7 mmol) was added and the mixture stirred 6h more. The slurry was evaporated under vacuum to remove most of the solvent and heptane (6 mL) added to the residue. The solid was collected by vacuum filtration and washed with heptane (2×5 mL) giving 8.01 g (68% yield) of the intermediate ethyl 6-chloro-2-methylpyrimidin-4-ylcarbamothioylcarbamate.

A solution of ethyl 6-chloro-2-methylpyrimidin-4-ylcarbamothioylcarbamate (275 mg, 1.0 mmol) and 1N sodium hydroxide (3.5 eq) was heated and stirred at 50° C. for 2h. The resulting slurry was cooled to 20-22° C. The solid was collected by vacuum filtration, washed with water, and dried to give 185 mg of 1-(6-chloro-2-methylpyrimidin-4-yl)thiourea (91% yield). $^1$H NMR (400 MHz, DMSO-$d_6$): δ2.51 (S, 3H), 7.05 (s, 1H), 9.35 (s,1H), 10.07 (s, 1H), 10.91 (s, 1H); $^{13}$C NMR (125 MHz, DMSO-d6) δ: 25.25, 104.56, 159.19, 159.33, 167.36, 180.91.

5B. (E)-N-(2-Chloro-6-methylphenyl)-3-ethoxyacrylamide

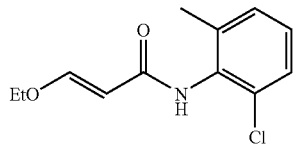

(5B)

To a cold stirring solution of 2-chloro-6-methylaniline (59.5 g 0.42 mol) and pyridine (68 ml, 0.63 mol) in THF (600 mL) was added 3-ethoxyacryloyl chloride (84.7 g, 0.63 mol) slowly keeping the temp at 0-5° C. The mixture was then warmed and stirred for 2 h. at 20° C. Hydrochloric acid (1N, 115 mL) was added at 0-10° C. The mixture was diluted with water (310 mL) and the resulting solution was concentrated under vacuum to a thick slurry. The slurry was diluted with toluene (275 mL) and stirred for 15 min. at 20-22° C. then 1 h. at 0° C. The solid was collected by vacuum filtration, washed with water (2×75 mL) and dried to give 74.1 g (73.6% yield) of (E)-N-(2-chloro-6-methylphenyl)-3-ethoxyacrylamide). $^1$H NMR (400 Hz, DMSO-$d_6$) δ 1.26 (t, 3H, J=7 Hz), 2.15 (s, 3H), 3.94 (q, 2H, J=7 Hz), 5.58 (d, 1H, J=12.4 Hz), 7.10-7.27 (m, 2H, J=7.5 Hz), 7.27-7.37 (d, 1H, J=7.5 Hz), 7.45(d, 1H, J=12.4 Hz), 9.28 (s, 1H); $^{13}$C NMR (100 MHz, CDCl$_3$) δ: 14.57, 18.96, 67.17, 97.99, 126.80, 127.44, 129.07, 131.32, 132.89, 138.25, 161.09, 165.36.

5C. 2-Amino-N-(2-chloro-6-methylphenyl)thiazole-5-carboxamide (5C)

To a mixture of compound 5B (5.00 g, 20.86 mmol) in 1,4-dioxane (27 mL) and water (27 mL) was added NBS (4.08 g, 22.9 mmol) at −10 to 0° C. The slurry was warmed and stirred at 20-22° C. for 3h. Thiourea (1.60 g, 21 mmol) was added and the mixture heated to 80° C. After 2h, the resulting solution was cooled to 20-22° and conc. ammonium hydroxide (4.2 mL) was added dropwise. The resulting slurry was concentrated under vacuum to about half volume and cooled to 0-5° C. The solid was collected by vacuum filtration, washed with cold water (10 mL), and dried to give 5.3 g (94.9% yield) of 2-amino-N-(2-chloro-6-methylphenyl)thiazole-5-carboxamide. $^1$H NMR (400 MHz, DMSO-$d_6$) δ δ 2.19 (s, 3H), 7.09-7.29 (m, 2H, J=7.5), 7.29-7.43 (d, 1H, J=7.5), 7.61 (s, 2H), 7.85 (s, 1H), 9.63 (s, 1H); $^{13}$C NMR (125 MHz, DMSO-d6) δ: 18.18, 120.63, 126.84, 127.90, 128.86, 132.41, 133.63, 138.76, 142.88, 159.45, 172.02.

5D. 2-(6-Chloro-2-methylpyrimidin-4-ylamino)-N-(2-chloro-6-methylphenyl)thiazole-5-carboxamide

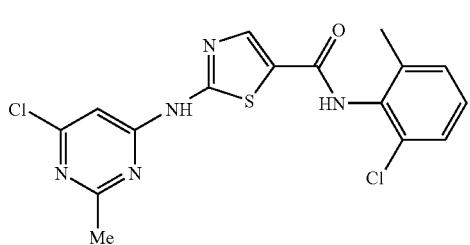

(5D)

To a stirring solution of compound 5C (5.00 g, 18.67 mmol) and 4,6-dichloro-2-methylpyrimidine (3.65 g, 22.4/mmol) in THF (65 mL) was added a 30% wt. solution of sodium t-butoxide in THF (21.1 g, 65.36 mmol) slowly with cooling to keep the temperature at 10-20° C. The mixture was stirred at room temperature for 1.5 h and cooled to 0-5° C. Hydrochloric acid, 2N (21.5 mL) was added slowly and the mixture stirred 1.75 h at 0-5° C. The solid was collected by vacuum filtration, washed with water (15 mL) and dried to give 6.63 g (86.4% yield) of compound 5D. $^1$H NMR (400 MHz, DMSO-$d_6$) δ 2.23 (s, 3H), 2.58 (s, 3H), 6.94 (s, 1H), 7.18-7.34, (m, 2H, J=7.5), 7.34-7.46 (d, 1H, J=7.5), 8.31 (s, 1H), 10.02 (s, 1H), 12.25 (s, 1H).

5E. Example 5

To a mixture of compound 5D (4.00 g, 10.14 mmol) and hydroxyethylpiperazine (6.60 g, 50.69 mmol) in n-butanol (40 mL) was added DIPEA (3.53 mL, 20.26 mmol). The slurry was heated at 118° C. for 4.5 h, then cooled slowly to room temperature. The solid was collected by vacuum filtration, washed with n-butanol (5 mL), and dried. The product (5.11 g) was dissolved in hot 80% EtOH—H$_2$O (80 mL), and the solution was clarified by filtration. The hot solution was slowly diluted with water (15 mL) and cooled slowly to room temperature. The solid was collected by vacuum filtration, washed with 50% ethanol-water (5 mL) and dried affording 4.27 g (83.2% yield) of N-(2-chloro-6-methylphenyl)-2-(6-(4-(3-hydroxyethyl)piperazin-1-yl)-2-methylpyrimidin-4-ylamino)thiazole-5-carboxamide as monohydrate. $^1$H NMR (400 MHz, DMSO-$d_6$) δ 2.23 (s, 3H), 2.40 (s, 3H), 2.42 (t, 2H, J=6), 2.48 (t, 4H, J=6.3), 3.50 (m, 4H), 3.53 (q, 2H, J=6), 4.45 (t, 1H, J=5.3), 6.04 (s, 1H), 7.25 (t, 1H, J=7.6), 7.27 (dd, 1H, J=7.6, 1.7), 7.40 (dd, 1H, J=7.6, 1.7), 8.21 (s, 1H), 9.87 (s, 1H), 11.47.

Example 6

Preparation of:

N-(2-chloro-6-methylphenyl)-2-(6-(4-(3-hydroxyethyl)piperazin-1-yl)-2-methylpyrimidin-4-ylamino)thiazole-5-carboxamide

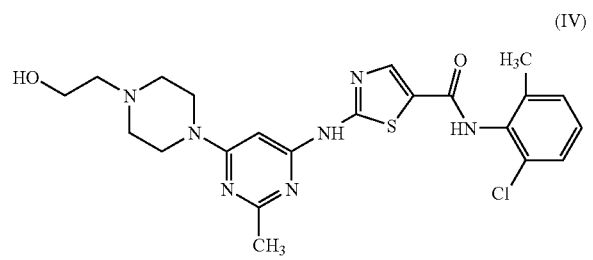

(IV)

To a slurry of (E)-N-(2-chloro-6-methylphenyl)-3-ethoxyacrylamide 5B (120 mg, 0.50 mmol) in THF (0.75 ml) and water (0.5 mL) was added NBS (98 mg, 0.55 mmol) at 0° C. The mixture was warmed and stirred at 20-22° C. for 3h. To this was added 1-(6-chloro-2-methylpyrimidin-4-yl)thiourea 5A (100 mg, 0.49 mmol), and the slurry heated and stirred at reflux for 2h. The slurry was cooled to 20-22° C. and the solid collected by vacuum filtration giving 140 mg (71% yield) of 2-(6-chloro-2-methylpyrimidin-4-ylamino)-N-(2-chloro-6-methylphenyl)thiazole-5-carboxamide 5D. $^1$H NMR (400 MHz, DMSO-$d_6$) δ 2.23 (s, 3H), 2.58 (s, 3H), 6.94 (s, 1H), 7.18-7.34, (m, 2H, J=7.5), 7.34-7.46 (d, 1H, J=7.5), 8.31 (s, 1H), 10.02 (s, 1H), 12.25 (s, 1H).

Compound 5D was elaborated to N-(2-chloro-6-methylphenyl)-2-(6-(4-(3-hydroxyethyl)piperazin-1-yl)-2-methylpyrimidin-4-ylamino)thiazole-5-carboxamide, following Step 5E.

Example 7

Preparation of:

N-(2-chloro-6-methylphenyl)-2-(6-(4-(3-hydroxyethyl)piperazin-1-yl)-2-methylpyrimidin-4-ylamino)thiazole-5-carboxamide

7A. 2-[4-(6-Chloro-2-methyl-pyrimidin-4-yl)-piperazin-1-yl]-ethanol

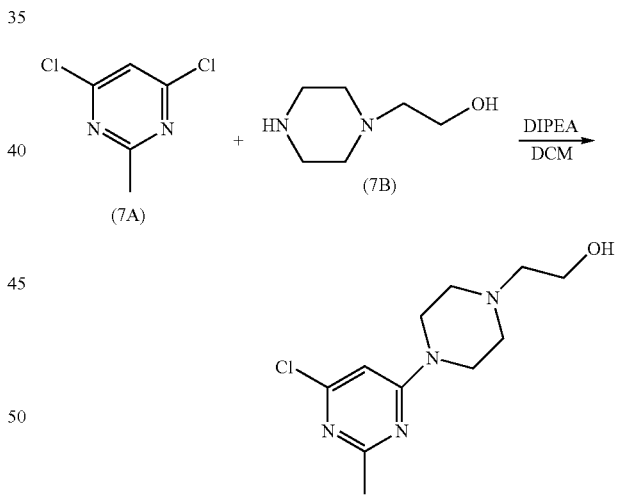

2-piperazin-1-yl-ethanol (8.2 g, 63.1 mmol) was added to a solution of 4,6-dichloro-2-methylpyrimidine (5.2 g, 31.9 mmol) in dichloromethane (80 ml) at rt. The mixture was stirred for two hours and triethylamine (0.9 ml) was added. The mixture was stirred at rt for 20h. The resultant solid was filtered. The cake was washed with dichloromethane (20 ml). The filtrate was concentrated to give an oil. This oil was dried under high vacuum for 20h to give a solid. This solid was stirred with heptane (50 ml) at rt for 5h. Filtration gave 7C (8.13 g) as a white solid

7B. Example 7

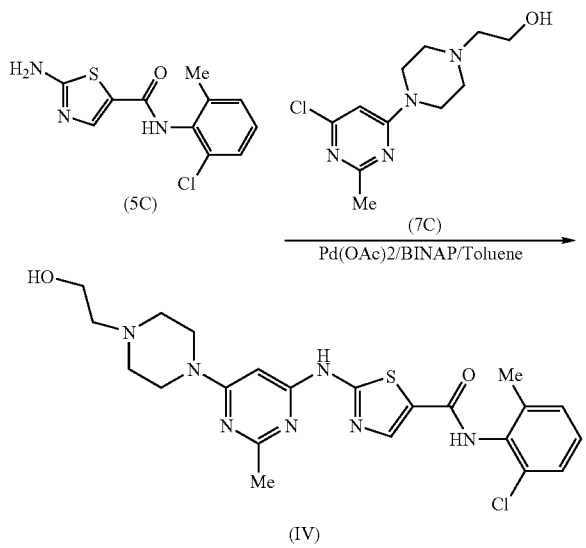

(IV)

To a 250 ml of round bottom flask were charged compound 5C (1.9 g, 7.1 mmol), compound 7C (1.5 g, 5.9 mmol), K$_2$CO$_3$ (16 g, 115.7 mmol), Pd (OAc)$_2$ (52 mg, 0.23 mmol) and BINAP (291 mg, 0.46 mmol). The flask was placed under vacuum and flushed with nitrogen. Toluene was added (60 ml). The suspension was heated to 100-110° C. and stirred at this temperature for 20h. After cooling to room temperature, the mixture was applied to a silica gel column. The column was first eluted with EtOAC, and then with 10% of MeOH in EtOAC. Finally, the column was washed with 10% 2M ammonia solution in MeOH/90% EtOAC. The fractions which contained the desired product were collected and concentrated to give compound IV as a yellow solid (2.3 g).

Analytical Methods

Solid State Nuclear Magnetic Resonance (SSNMR)

All solid-state C-13 NMR measurements were made with a Bruker DSX-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (A. E. Bennett et al, *J. Chem. Phys.*, 1995, 103, 6951), (G. Metz, X. Wu and S. O. Smith, *J. Magn. Reson. A.*, 1994, 110, 219-227). Approximately 70 mg of sample, packed into a canister-design zirconia rotor was used for each experiment. Chemical shifts (δ) were referenced to external adamantane with the high frequency resonance being set to 38.56 ppm (W. L. Earl and D. L. Vander-Hart, *J. Magn. Reson.*, 1982, 48, 35-54).

X-Ray Powder Diffraction

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

X-Ray powder diffraction data for the crystalline forms of Compound (IV) were obtained using a Bruker GADDS (BRUKER AXS, Inc., 5465 East Cheryl Parkway Madison, Wis. 53711 USA) (General Area Detector Diffraction System) manual chi platform goniometer. Powder samples were placed in thin walled glass capillaries of 1 mm or less in diameter; the capillary was rotated during data collection. The sample-detector distance was 17 cm. The radiation was Cu Kα (45 kV 111 mA, λ=1.5418 Å). Data were collected for 3<2θ<35° with a sample exposure time of at least 300 seconds.

Single Crystal X-Ray

All single crystal data were collected on a Bruker-Nonius (BRUKER AXS, Inc., 5465 East Cheryl Parkway Madison, Wis. 53711 USA) Kappa CCD 2000 system using Cu Kα radiation (λ=1.5418 Å) and were corrected only for the Lorentz-polarization factors. Indexing and processing of the measured intensity data were carried out with the HKL2000 software package (Otwinowski, Z. & Minor, W. (1997) in *Macromolecular Crystallography*, eds. Carter, W. C. Jr & Sweet, R. M. (Academic, NY), Vol. 276, pp. 307-326) in the Collect program suite (Data collection and processing user interface: Collect: Data collection software, R. Hooft, Nonius B. V., 1998).

The structures were solved by direct methods and refined on the basis of observed reflections using either the SDP (SDP, Structure Determination Package, Enraf-Nonius, Bohemia NY 11716 Scattering factors, including f' and f", in the SDP software were taken from the "International Tables for Crystallography", Kynoch Press, Birmingham, England, 1974; Vol IV, Tables 2.2A and 2.3.1) software package with minor local modifications or the crystallographic package, MAXUS (maXus solution and refinement software suite: S. Mackay, C. J. Gilmore, C. Edwards, M. Tremayne, N. Stewart, K. Shankland. maXus: a computer program for the solution and refinement of crystal structures from diffraction data).

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w = [\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w = [\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied Differential Scanning Calorimetry The DSC instrument used to test the crystalline forms was a TA Instruments® model Q1000. The DSC cell/sample chamber was purged with 100 ml/min of ultra-high purity nitrogen gas. The instrument was calibrated with high purity indium. The accuracy of the measured sample temperature with this method is within about +/−1° C., and the heat of fusion can be measured within a relative error of about +/−5%. The sample was placed into an open aluminum DSC pan and measured against an empty reference pan. At least 2 mg of sample powder was placed into the bottom of the pan and lightly tapped down to ensure good contact with the pan. The weight of the sample was measured accurately and recorded to a hundredth of a milligram. The instrument was programmed to heat at 10° C. per minute in the temperature range between 25 and 350° C.

The heat flow, which was normalized by a sample weight, was plotted versus the measured sample temperature. The data were reported in units of watts/gram ("W/g"). The plot was made with the endothermic peaks pointing down. The endothermic melt peak was evaluated for extrapolated onset temperature, peak temperature, and heat of fusion in this analysis.

Thermogravimetric Analysis (TGA)

The TGA instrument used to test the crystalline forms was a TAInstruments® model Q500. Samples of at least 10 milligrams were analyzed at a heating rate of 10° C. per minute in the temperature range between 25° C. and about 350° C.

Example 8

Preparation of:

crystalline monohydrate of N-(2-chloro-6-methylphenyl)-2-(6-(4-(3-hydroxyethyl)piperazin-1-yl)-2-methylpyrimidin-4-ylamino)thiazole-5-carboxamide (IV)

An example of the crystallization procedure to obtain the crystalline monohydrate form is shown here:

Charge 48 g of the compound of formula (IV).

Charge approximately 1056 mL (22 mL/g) of ethyl alcohol, or other suitable alcohol.

Charge approximately 144 mL of water.

Dissolve the suspension by heating to approximately 75° C.

Optional: Polish filter by transfer the compound of formula (IV) solution at 75° C. through the preheated filter and into the receiver.

Rinse the dissolution reactor and transfer lines with a mixture of 43 mL of ethanol and 5 mL of water.

Heat the contents in the receiver to 75-80° C. and maintain 75-80° C. to achieve complete dissolution.

Charge approximately 384 mL of water at a rate such that the batch temperature is maintained between 75-80° C.

Cool to 75° C., and, optionally, charge monohydrate seed crystals. Seed crystals are not essential to obtaining monohydrate, but provide better control of the crystallization.

Cool to 70° C. and maintain 70° C. for ca. 1 h.

Cool from 70 to 5 C over 2 h, and maintain the temperature between 0 at 5° C. for at least 2 h.

Filter the crystal slurry.

Wash the filter cake with a mixture of 96 mL of ethanol and 96 mL of water.

Dry the material at ≦50° C. under reduced pressure until the water content is 3.4 to 4.1% by KF to afford 41 g (85 M %).

Alternately, the monohydrate can be obtained by:

1) An aqueous solution of the acetate salt of compound IV was seeded with monohydrate and heated at 80° C. to give bulk monohydrate.

2) An aqueous solution of the acetate salt of compound IV was seeded with monohydrate. On standing several days at room temperature, bulk monohydrate had formed.

3) An aqueous suspension of compound IV was seeded with monohydrate and heated at 70° C. for 4 hours to give bulk monohydrate. In the absence of seeding, an aqueous slurry of compound IV was unchanged after 82 days at room temperature.

4) A solution of compound IV in a solvent such as NMP or DMA was treated with water until the solution became cloudy and was held at 75-85° C. for several hours. Monohydrate was isolated after cooling and filtering.

5) A solution of compound IV in ethanol, butanol, and water was heated. Seeds of monohydrate were added to the hot solution and then cooled. Monohydrate was isolated upon cooling and filtration.

One of ordinary skill in the art will appreciate that the monohydrate of the compound of formula (IV) may be represented by the XRPD as shown in FIG. 1 or by a representative sampling of peaks as shown in Table 1.

Representative peaks taken from the XRPD of the monohydrate of the compound of formula (IV) are shown in Table 1.

TABLE 1

| 2-Theta | d(Å) | Height |
|---|---|---|
| 17.994 | 4.9257 | 915 |
| 18.440 | 4.8075 | 338 |
| 19.153 | 4.6301 | 644 |
| 19.599 | 4.5258 | 361 |
| 21.252 | 4.1774 | 148 |
| 24.462 | 3.6359 | 250 |
| 25.901 | 3.4371 | 133 |
| 28.052 | 3.1782 | 153 |

The XRPD is also characterized by the following list comprising 2θ values selected from the group consisting of: 4.6±0.2, 11.2±0.2, 13.8±0.2, 15.2±0.2, 17.9±0.2, 19.1±0.2, 19.6±0.2, 23.2±0.2, 23.6±0.2. The XRPD is also characterized by the list of 2θ values selected from the group consisting of: 18.0±0.2, 18.4±0.2, 19.2±0.2, 19.6±0.2, 21.2±0.2, 24.5±0.2, 25.9±0.2, and 28.0±0.2.

Single crystal x-ray data was obtained at room temperature (+25° C.). The molecular structure was confirmed as a monohydrate form of the compound of Formula (IV).

The following unit cell parameters were obtained for the monohydrate of the compound of formula (IV) from the x-ray analysis at 25° C.:

a(Å)=13.8632(7); b(Å)=9.3307(3); c(Å)=38.390(2);

V(Å$^3$) 4965.9(4); Z'=1; Vm=621

Space group Pbca

Molecules/unit cell 8

Density (calculated) (g/cm$^3$) 1.354

Wherein Z'=number of drug molecules per asymmetric unit. Vm=V(unit cell)/(Z drug molecules per cell).

Single crystal x-ray data was also obtained at −50° C. The monohydrate form of the compound of Formula (IV) is characterized by unit cell parameters approximately equal to the following:

Cell dimensions:
a(Å)=13.862(1);
b(Å)=9.286(1);
c(Å)=38.143(2);
Volume=4910(1) Å$^3$
Space group Pbca
Molecules/unit cell 8
Density (calculated) (g/cm$^3$) 1.369 wherein the compound is at a temperature of about −50° C.

The simulated XRPD was calculated from the refined atomic parameters at room temperature.

The monohydrate of the compound of formula (IV) is represented by the DSC as shown in FIG. 2. The DSC is characterized by a broad peak between approximately 95° C. and 130° C. This peak is broad and variable and corresponds to the loss of one water of hydration as seen in the TGA graph. The DSC also has a characteristic peak at approximately 287° C. which corresponds to the melt of the dehydrated form of the compound of formula (IV).

The TGA for the monohydrate of the compound of Formula (IV) is shown in FIG. 2 along with the DSC. The TGA shows a 3.48% weight loss from 50° C. to 175° C. The weight loss corresponds to a loss of one water of hydration from the compound of Formula (IV).

The monohydrate may also be prepared by crystallizing from alcoholic solvents, such as methanol, ethanol, propanol, i-propanol, butanol, pentanol, and water.

Example 9

Preparation of:

crystalline n-butanol solvate of N-(2-chloro-6-methylphenyl)-2-(6-(4-(3-hydroxyethyl)piperazin-1-yl)-2-methylpyrimidin-4-ylamino)thiazole-5-carboxamide (IV)

The crystalline butanol solvate of the compound of formula (IV) is prepared by dissolving compound (IV) in 1-butanol at reflux (116-118° C.) at a concentration of approximately 1 g/25 mL of solvent. Upon cooling, the butanol solvate crystallizes out of solution. Filter, wash with butanol, and dry.

The following unit cell parameters were obtained from the x-ray analysis for the crystalline butanol solvate, obtained at room temperature:

a(Å)=22.8102(6); b(Å)=8.4691(3); c(Å)=15.1436(5); β=95.794(2);
V(Å$^3$) 2910.5(2); Z'=1; Vm=728
Space group P2$_1$/a
Molecules/unit cell 4
Density (calculated) (g/cm$^3$) 1.283

Wherein Z'=number of drug molecules per asymmetric unit. Vm=V(unit cell)/(Z drug molecules per cell).

Figure 3:
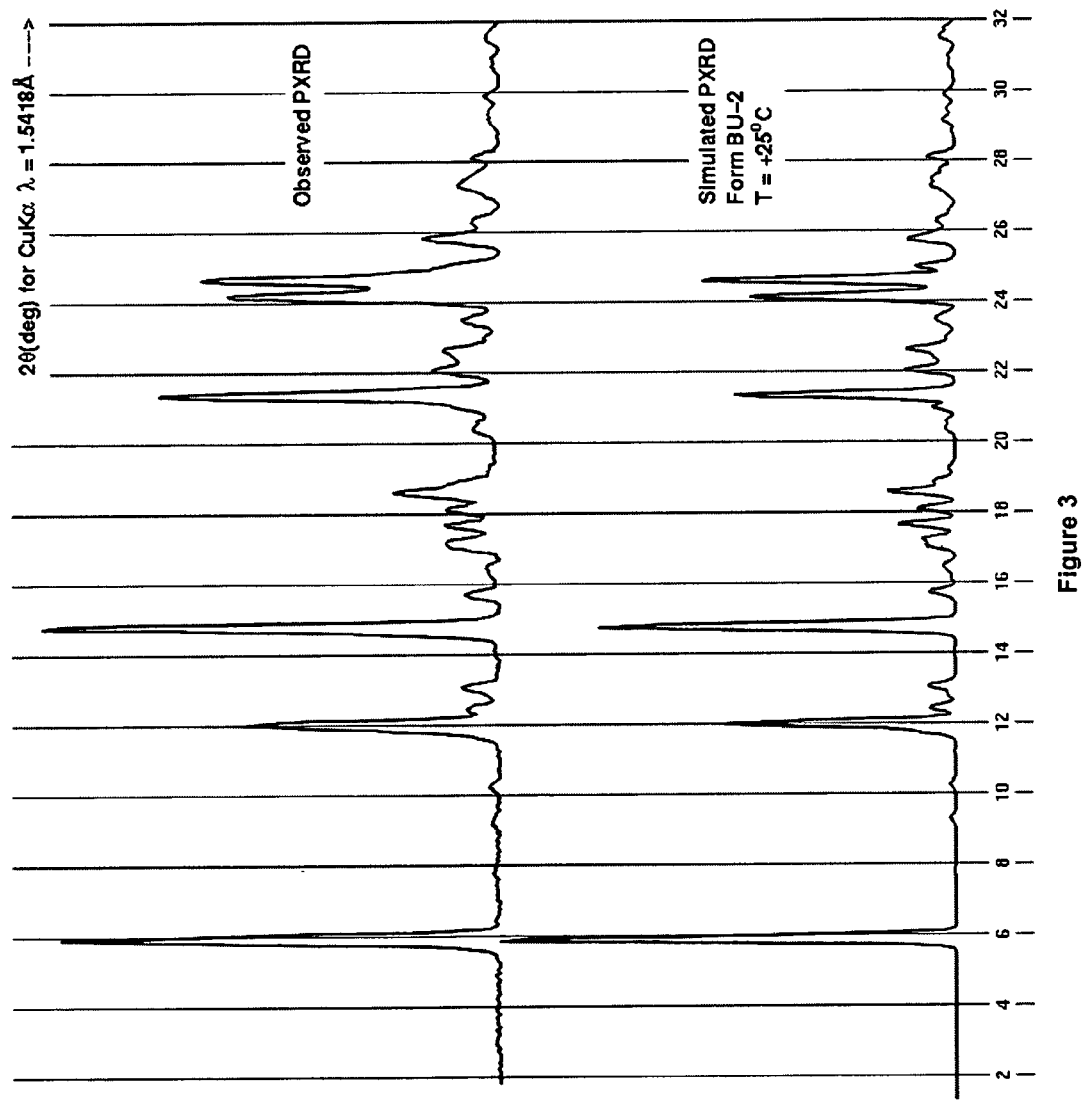
FIG. 3 shows a simulated (bottom) (from atomic parameters refined at room temperature) and experimental (top) pXRD patterns for crystalline butanol solvate of the compound of formula (IV).

One of ordinary skill in the art will appreciate that the butanol solvate of the compound of formula (IV) may be represented by the XRPD as shown in FIG. 3 or by a representative sampling of peaks. Representative peaks for the crystalline butanol solvate are 2θ values of: 5.9±0.2, 12.0±0.2, 13.0±0.2, 17.7±0.2, 24.1±0.2, and 24.6±0.2.

Example 10

Preparation of:

crystalline ethanol solvate of N-(2-chloro-6-methylphenyl)-2-(6-(4-(3-hydroxyethyl)piperazin-1-yl)-2-methylpyrimidin-4-ylamino)thiazole-5-carboxamide (IV)

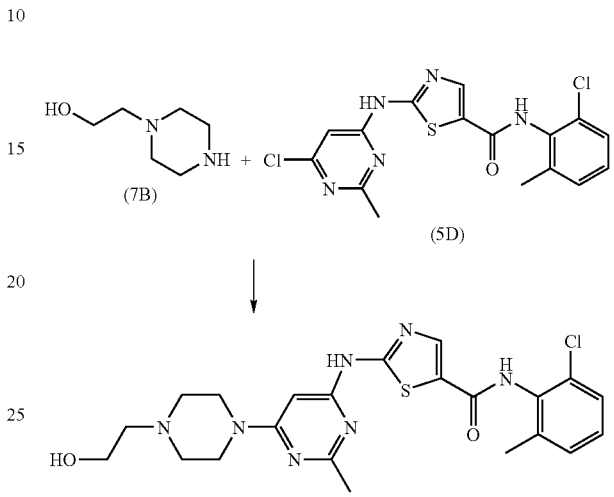

To a 100-mL round bottom flask was charged 4.00 g (10.1 mmol) of 5D (contained 2.3 Area % 5C) 6.60 g (50.7 mmol) of 7B, 80 mL of n-butanol and 2.61 g (20.2 mmol) of DIPEA. The resulting slurry was heated to 120° C. and maintained at 120° C. for 4.5 h whereby HPLC analysis showed 0.19 relative Area % of residual 5D to compound IV. The homogeneous mixture was cooled to 20° C. and left stirring overnight. The resulting crystals were filtered. The wet cake was washed twice with 10-mL portions of n-butanol to afford a white crystalline product. HPLC analysis showed this material to contain 99.7 Area % compound IV and 0.3 Area % 5C.

The resulting wet cake was returned to the 100-mL reactor, and charged with 56 mL (12 mL/g) of 200 proof ethanol. At 80° C. an additional 25 mL of ethanol was added. To this mixture was added 10 mL of water resulting in rapid dissolution. Heat was removed and crystallization was observed at 75-77° C. The crystal slurry was further cooled to 20° C. and filtered. The wet cake was washed once with 10 mL of 1:1 ethanol: water and once with 10 mL of n-heptane. The wet cake contained 1.0% water by KF and 8.10% volatiles by LOD. The material was dried at 60° C./30 in Hg for 17 h to afford 3.55 g (70 M %) of material containing only 0.19% water by KF, 99.87 Area % by HPLC. The $^1$H NMR spectrum, however revealed that the ethanol solvate had been formed.

The following unit cell parameters were obtained from the x-ray analysis for the crystalline ethanol solvate (di-ethanolate, E2-1), obtained at −40° C.:

a(Å)=22.076(1); b(Å)=8.9612(2); c(Å)=16.8764(3); β=114.783(1);
V(Å$^3$) 3031.1(1); Z'=1; Vm=758
Space group P2$_1$/a
Molecules/unit cell 4
Density (calculated) (g/cm$^3$) 1.271

Wherein Z'=number of drug molecules per asymmetric unit. Vm=V(unit cell)/(Z drug molecules per cell).

Figure 4:
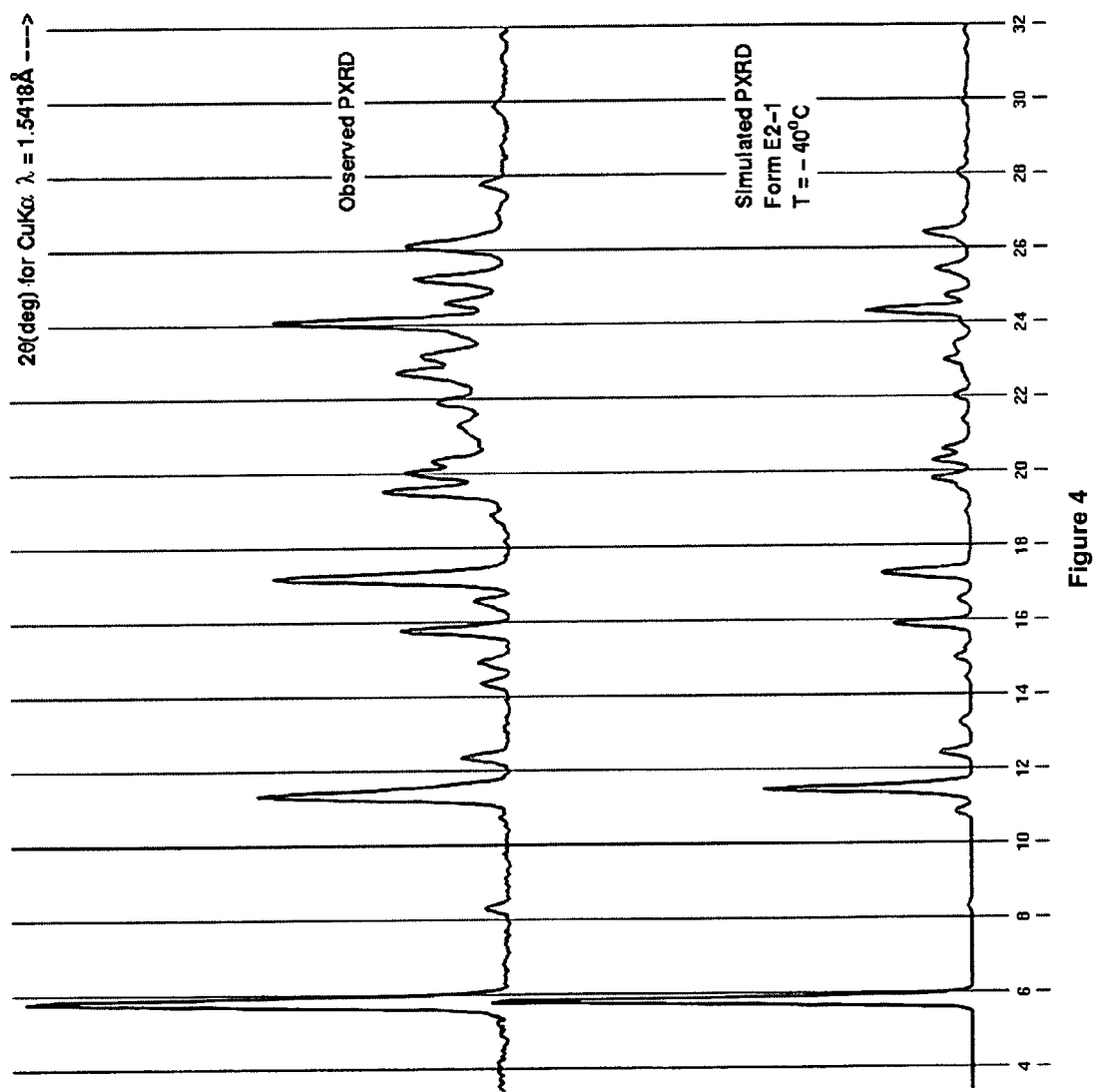
FIG. 4 shows a simulated (bottom) (from atomic parameters refined at −40° C.) and experimental (top) pXRD patterns for crystalline ethanol solvate of the compound of formula (IV).

One of ordinary skill in the art will appreciate that the ethanol solvate (E2-1) of the compound of formula (IV) may be represented by the XRPD as shown in FIG. 4 or by a representative sampling of peaks. Representative peaks for the crystalline ethanol solvate are 2θ values of: 5.8±0.2, 11.3±0.2, 15.8±0.2, 17.2±0.2, 19.5±0.2, 24.1±0.2, 25.3±0.2, and 26.2±0.2.

In addition, during the process to form the ethanolate (diethanolate) the formation of another ethanol solvate (½ ethanolate, T1E2-1) has been observed. To date this additional ethaonol solvate is known strictly as a partial desolvation product of the original diethanolate form E2-1, and has only been observed on occasion during crystallization of E2-1

The following unit cell parameters were obtained from the x-ray analysis for the crystalline ½ ethanol solvate T1E2-1, obtained at −10° C.:

a(Å)=22.03(2); b(Å)=9.20(1); c(Å)=12.31(1);
β=93.49(6)
V(Å$^3$) 2491(4)); Z'=1; Vm=623;
Space group P2$_1$/a
Molecules/unit cell 4
Density (calculated) (g/cm$^3$) 1.363

Wherein Z'=number of drug molecules per asymmetric unit. Vm=V(unit cell)/(Z drug molecules per cell).

One of ordinary skill in the art will appreciate that the ethanol solvate (T1E2-1) of the compound of formula (IV) may be represented by the XRPD as shown in FIG. 7 or by a representative sampling of peaks. Representative peaks for the crystalline ethanol solvate are 2θ values of: 7.20±0.2, 12.01±0.2, 12.81±0.2, 18.06±0.2, 19.30±0.2, and 25.24±0.2.

Example 11

Preparation of:

crystalline N-(2-chloro-6-methylphenyl)-2-(6-(4-(3-hydroxyethyl)piperazin-1-yl)-2-methylpyrimidin-4-ylamino)thiazole-5-carboxamide (IV) (Neat form N-6)

To a mixture of compound 5D (175.45 g, 0.445 mol) and hydroxyethylpiperazine (289.67 g, 2.225 mol) in NMP (1168 mL) was added DIPEA (155 mL, 0.89 mol). The suspension was heated at 110° C. (solution obtained) for 25 min., then cooled to about 90° C. The resulting hot solution was added dropwise into hot (80° C.) water (8010) mL, keeping the temperature at about 80° C. The resulting suspension was stirred 15 min at 80° C. then cooled slowly to room temperature. The solid was collected by vacuum filtration, washed with water (2×1600 mL) and dried in vacuo at 55-60° C. affording 192.45 g (88.7% yield) of N-(2-chloro-6-methylphenyl)-2-(6-(4-(3-hydroxyethyl)piperazin-1-yl)-2-methylpyrimidin-4-ylamino)thiazole-5-carboxamide. $^1$H NMR (400 MHz, DMSO-d$_6$): δ 2.24 (s, 3H), 2.41 (s, 3H), 2.43 (t, 2H, J=6), 2.49 (t, 4H, J=6.3), 3.51 (m, 4H), 3.54 (q, 2H, J=6), 4.46 (t, 1H, J=5.3), 6.05 (s, 1H), 7.26 (t, 1H, J=7.6), 7.28 (dd, 1H, J=7.6, 1.7), 7.41 (dd, 1H, J=7.6, 1.7), 8.23 (s, 1H), 9.89 (s, 1H), 11.48. KF0.84; DSC: 285.25° C. (onset), 286.28° C. (max).

The following unit cell parameters were obtained from the x-ray analysis for the neat crystalline compound IV, obtained at 23° C.:

a(Å)=22.957(1); b(Å)=8.5830(5); c(Å)=13.803(3); β=112.039(6);
V(Å$^3$)=2521.0(5); Z'=1; Vm=630
Space group P2$_1$/a
Molecules/unit cell 4
Density (calculated) (g/cm$^3$) 1.286

Wherein Z'=number of drug molecules per asymmetric unit. Vm=V(unit cell)/(Z drug molecules per cell).

Figure 5:
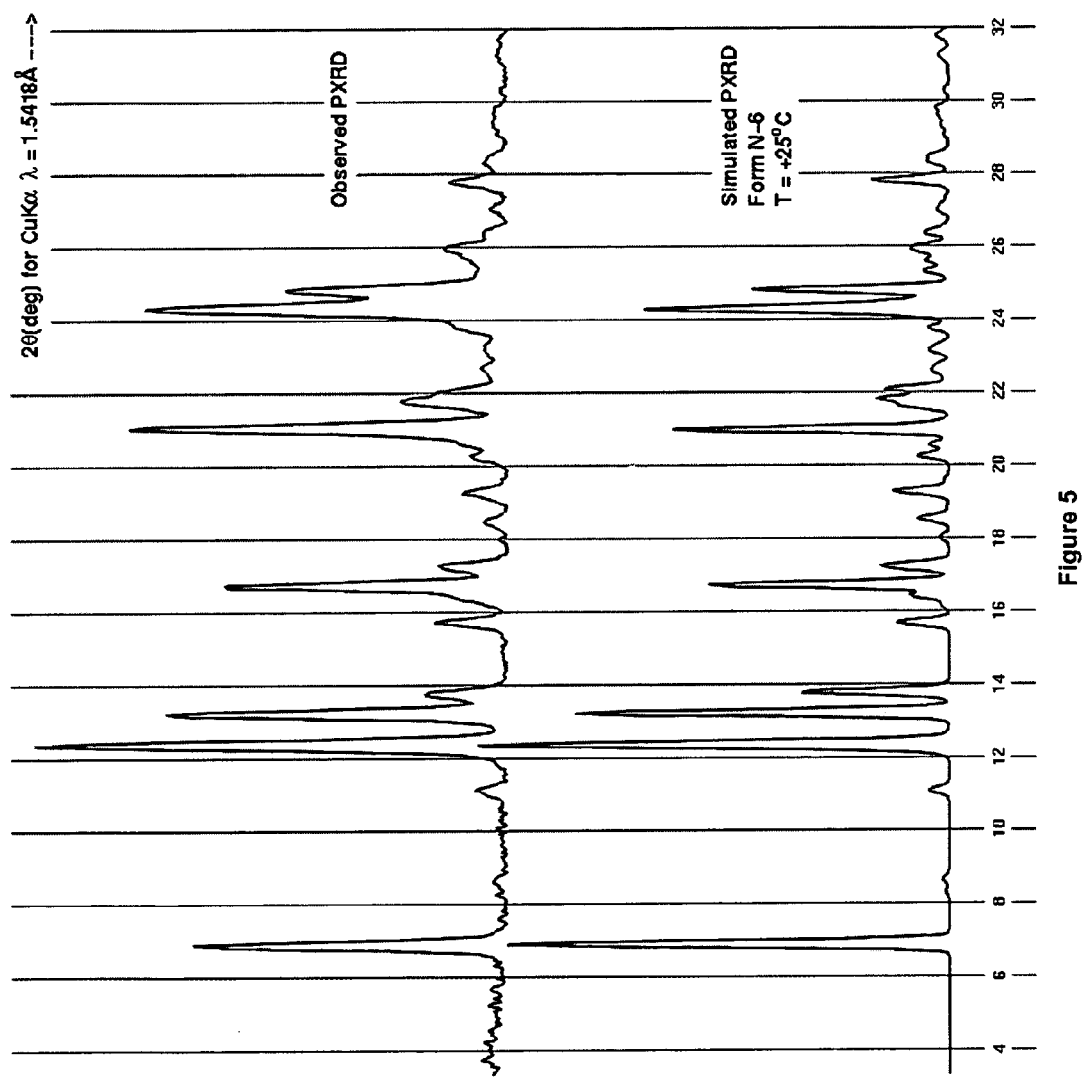
FIG. 5 shows a simulated (bottom) (from atomic parameters refined at room temperature) and experimental (top) pXRD patterns for crystalline neat form (N-6) of the compound of formula (IV).

One of ordinary skill in the art will appreciate that the crystalline form of the compound of formula (IV) may be represented by the XRPD as shown in FIG. 5 or by a representative sampling of peaks. Representative peaks for the crystalline neat form (N-6) are 2θ values of: 6.8±0.2, 11.1±0.2, 12.3±0.2, 13.2±0.2, 13.7±0.2, 16.7±0.2, 21.0±0.2, 24.3±0.2, and 24.8±0.2.

Example 12

Preparation of:

crystalline N-(2-chloro-6-methylphenyl)-2-(6-(4-(3-hydroxyethyl)piperazin-1-yl)-2-methylpyrimidin-4-ylamino)thiazole-5-carboxamide (IV) (neatform T1H1-7)

The title neat form may be prepared by heating the monohydrate form of the compound of formula (IV) above the dehydration temperature.

The following unit cell parameters were obtained from the x-ray analysis for the neat crystalline (T1H1-7) compound IV, obtained at 25° C.:

a(Å)=13.4916; b(Å)=9.3992(2); c(Å)=38.817(1);
V(Å$^3$)=4922.4(3); Z'=1; Vm=615
Space group Pbca
Density (calculated) (g/cm$^3$) 1.317

Wherein Z'=number of drug molecules per asymmetric unit. Vm=V(unit cell)/(Z drug molecules per cell).

Figure 6:
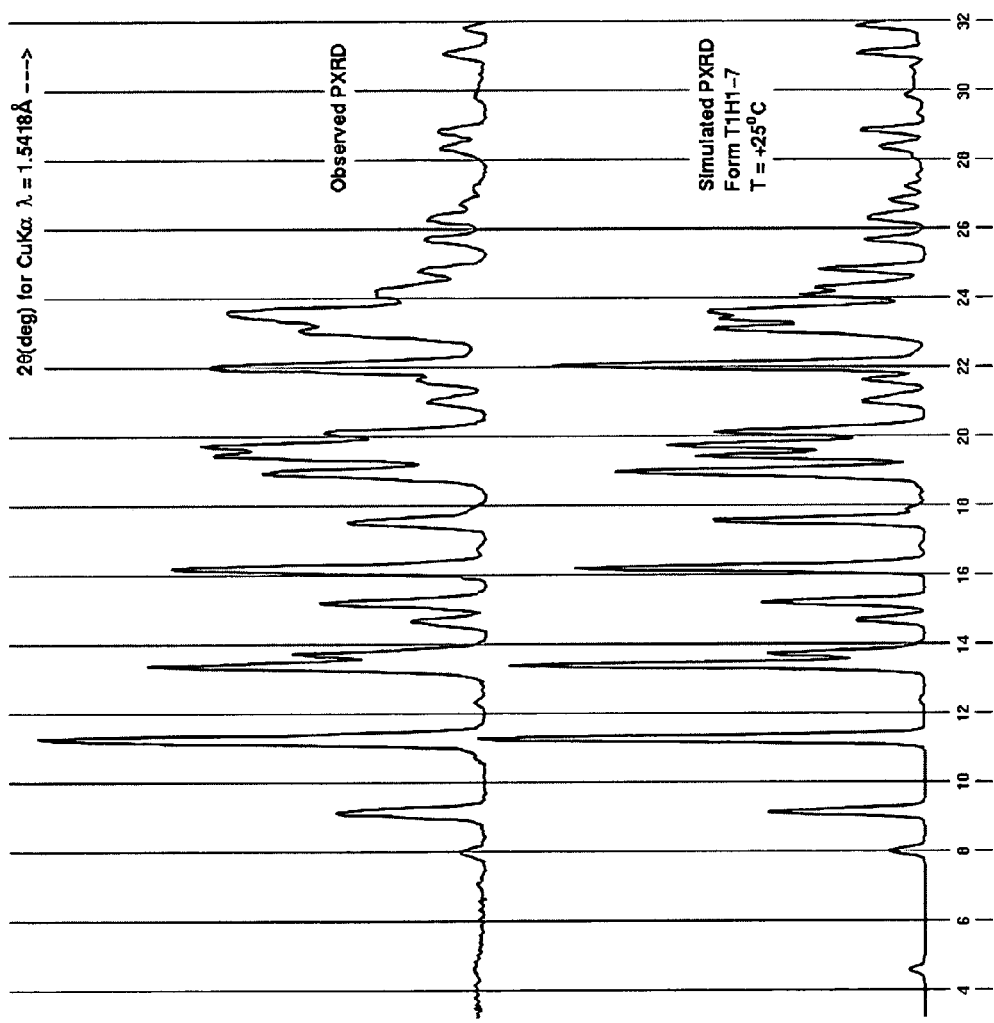
FIG. 6 shows a simulated (bottom) (from atomic parameters refined at room temperature) and experimental (top) pXRD patterns for crystalline neat form (T1H1-7) of the compound of formula (IV).

One of ordinary skill in the art will appreciate that the neat crystalline form (T1H1-7) of the compound of formula (IV) may be represented by the XRPD as shown in FIG. 6 or by a representative sampling of peaks. Representative peaks for the crystalline neat form (T1H1-7)) are 2θ values of: 8.0±0.2, 9.7±0.2, 11.2±0.2, 13.3±0.2, 17.5±0.2, 18.9±0.2, 21.0±0.2, 22.0±0.2.

Obviously, numerous modifications and variations of the present invention are possible in light of the above teachings. It is therefore to be understood that within the scope of the appended claims, the invention may be practiced otherwise than as specifically described herein.

What we claim is:

1. Crystalline monohydrate of the compound of formula (IV)

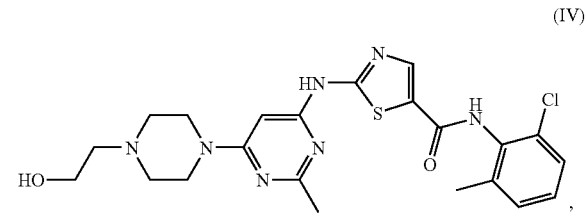

(IV)

which is characterized by an x-ray powder diffraction pattern substantially in accordance with that shown in FIG. 1.

2. The compound of claim 1, which is characterized by differential scanning calorimetry thermogram and a thermogravimetric anaylsis substantially in accordance with that shown in FIG. 2.

3. Crystalline monohydrate of the compound of formula (IV)

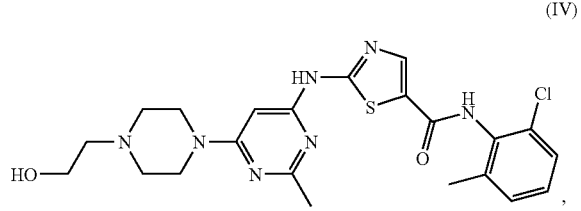

(IV)

which is characterized by an x-ray powder diffraction pattern (CuKα γ=1.5418 Å at a temperature of about 23° C.) comprising four or more 2θ values selected from the group consisting of: 18.0±0.2, 18.4±0.2, 19.2±0.2, 19.6±0.2, 21.2±0.2, 24.5±0.2, 25.9±0.2, and 28.0±0.2.

4. A solid pharmaceutical composition comprising a therapeutically effective amount of the compound of claim 3 and a pharmaceutically acceptable carrier.

5. The compound of claim 3, characterized by unit cell parameters approximately equal to the following:
Cell dimensions:
 a(Å)=13.8632(7);
 b(Å)=9.3307(3);
 c(Å)=38.390(2);
Volume=4965.9(4) Å$^3$
Space group Pbca
Molecules/unit cell 8
Density (calculated) (g/cm$^3$) 1.354.

6. A process for preparing the compound of claim 3 comprising heating and dissolving the compound of formula (IV) in an ethanol/water mixture and crystallizing the monohydrate from the ethanol/water mixture as it cools.

7. The process of claim 6, wherein a butanol solvate of the compound of formula (IV) is dissolved in the ethanol/water mixture.

8. The compound of claim 3, wherein the compound is substantially pure.

9. The compound of claim 3, the compound being further characterized by a differential scanning calorimetry having a broad peak between approximately 95° C. and 13° C. which corresponds to the loss of one water of hydration on thermogravitmetric analysis.

10. The compound of claim 9, which is further characterized by a weight loss of 3.48% by thermogravimetric analysis between 50° C. and 175° C.

11. The compound of claim 9, wherein the differential scanning calorimetry further has a peak at approximately 287° C.

12. Crystalline monohydrate of the compound of formula (IV)

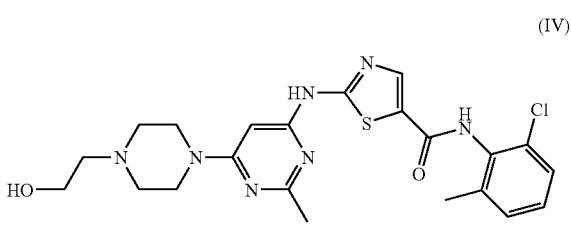

(IV)

which is characterized by a differential scanning calorimetry having a broad peak between approximately 95° C. and 130° C. which corresponds to the loss of one water of hydration on thermogravitmetric analysis.

13. A solid pharmaceutical composition comprising a therapeutically effective amount of the compound of claim 12 and a pharmaceutically acceptable carrier.

14. A solid pharmaceutical composition comprising a therapeutically effective amount of the compound of claim 9 and a pharmaceutically acceptable carrier.

15. The compound of claim 12, wherein the compound is substantially pure.

16. The compound of claim 9, wherein the compound is substantially pure.

* * * * *

UNITED STATES PATENT AND TRADEMARK OFFICE
CERTIFICATE OF CORRECTION

PATENT NO. : 7,491,725 B2  Page 1 of 1
APPLICATION NO. : 11/192867
DATED : February 17, 2009
INVENTOR(S) : Lajeunesse et al.

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 251 days.

Delete the phrase "by 251 days" and insert -- by 214 days --

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,491,725 B2 | Page 1 of 1 |
| APPLICATION NO. | : 11/192867 | |
| DATED | : February 17, 2009 | |
| INVENTOR(S) | : LaJeunesse et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 417 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,491,725 B2
APPLICATION NO. : 11/192867
DATED : February 17, 2009
INVENTOR(S) : Jean Lajeunesse et al.

Page 1 of 1

It is certified that error appears in the above-identified patent and that said Letters Patent is hereby corrected as shown below:

On the Title Page

On the Title Page, Column 2, OTHER PUBLICATIONS, line 23, delete "AMinothioacryloyl" and insert -- Aminothioacrylolyl --.

In the Claims:

Column 48, line 66, Claim 2, delete "anaylsis" and insert -- analysis --.

Column 49, line 15, Claim 3, delete "$\gamma$" and insert -- $\lambda$ --.

Column 50, line 3, Claim 9, delete "13°" and insert -- 130° --.

Column 50, lines 4 to 5, Claim 9, delete "thermo-gravitmetric" and insert -- thermogravimetric --.

Column 50, line 28, Claim 12, delete "thermogravitmetric" and insert -- thermogravimetric --.

Signed and Sealed this
Thirteenth Day of December, 2011

David J. Kappos
*Director of the United States Patent and Trademark Office*